(12) United States Patent  
Miller

(10) Patent No.: US 6,475,139 B1  
(45) Date of Patent: Nov. 5, 2002

(54) VISUALLY-DIRECTED SURGICAL INSTRUMENT AND METHOD FOR TREATING FEMALE URINARY INCONTINENCE

(75) Inventor: Gary H. Miller, Milpitas, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/573,645

(22) Filed: May 18, 2000

Related U.S. Application Data

(60) Provisional application No. 60/138,231, filed on Jun. 9, 1999.

(51) Int. Cl.[7] .............................................. A61B 1/307
(52) U.S. Cl. ........................... 600/135; 600/29; 600/37
(58) Field of Search ................................ 600/135, 114, 600/101, 138, 129, 29, 30, 37; 606/119, 139; 604/515

(56) References Cited

U.S. PATENT DOCUMENTS

| | | | | | |
|---|---|---|---|---|---|
| 3,372,695 | A | * | 3/1968 | Beliveau et al. | 600/29 |
| 4,392,495 | A | * | 7/1983 | Bayers | 128/898 |
| 5,013,292 | A | * | 5/1991 | Lemay | 600/30 |
| 5,112,344 | A | * | 5/1992 | Petros | 600/30 |
| 5,362,294 | A | * | 11/1994 | Seitzinger | 600/37 |
| 5,855,549 | A | * | 1/1999 | Newman | 600/105 |
| 5,899,909 | A | * | 5/1999 | Claren et al. | 606/118 |
| 5,997,554 | A | | 12/1999 | Thompson | |
| 6,030,393 | A | * | 2/2000 | Corlew | 606/148 |
| 6,273,852 | B1 | * | 8/2001 | Lehe et al. | 600/30 |
| 2001/0049467 | A1 | * | 12/2001 | Lehe et al. | 600/30 |

* cited by examiner

Primary Examiner—Linda C. M. Dvorak
Assistant Examiner—Jocelyn Ram

(57) ABSTRACT

Described is a surgical instrument and method for treating female urinary stress incontinence. The instrument includes a curved needle-like element defining in part a curved shaft having a distal end and a proximal end. A tape attaches to the needle for implanting into the lower abdomen of a female to provide support to the urethra. The needle defines an inner lumen for passage of optical devices and/or fluids. A surgical optical system may interface directly with the needle, or alternatively, the needle hand piece or handle may be modified to accept the optical system. The tip of the needle is also modified to contain a window or viewing port that allows for the transmission of light from the ambient target tissue into the imaging lens of the optical system. The optical system allows the surgeon to maintain continuous anatomic visualization during introduction and navigation of the needle within the lower abdomen.

16 Claims, 26 Drawing Sheets

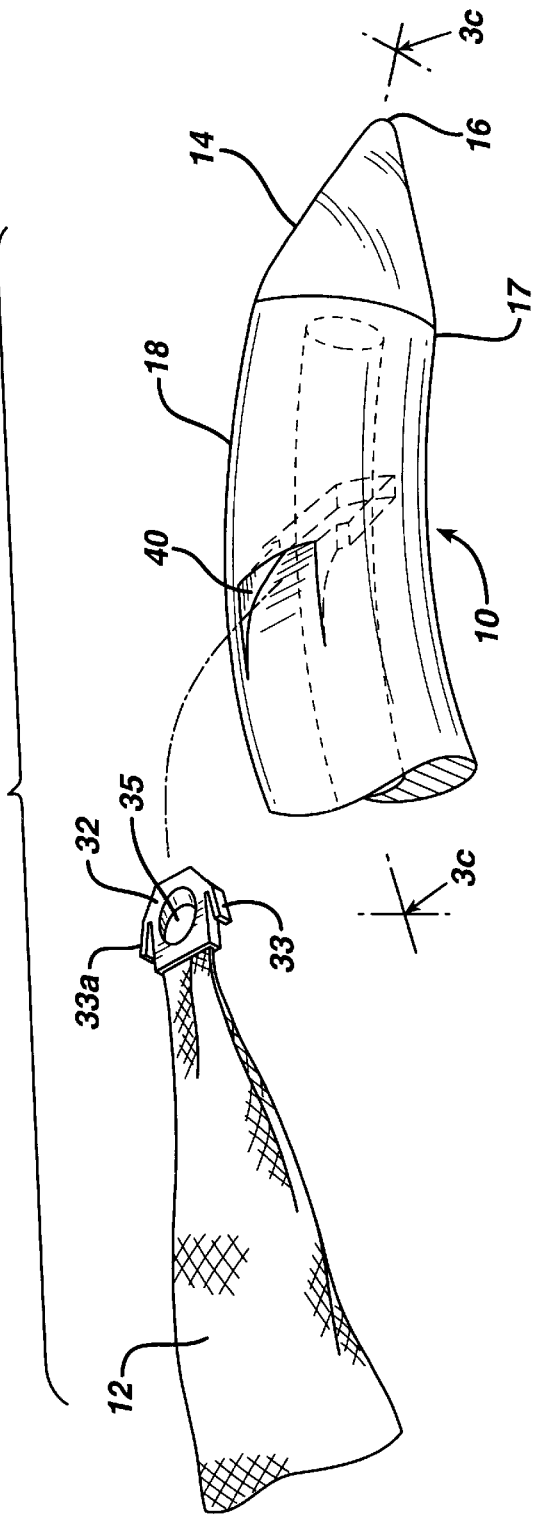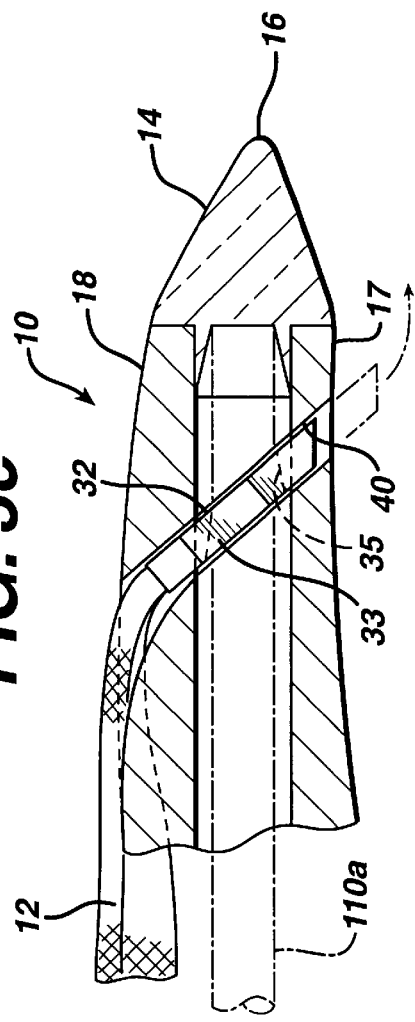
FIG. 3b
FIG. 3c

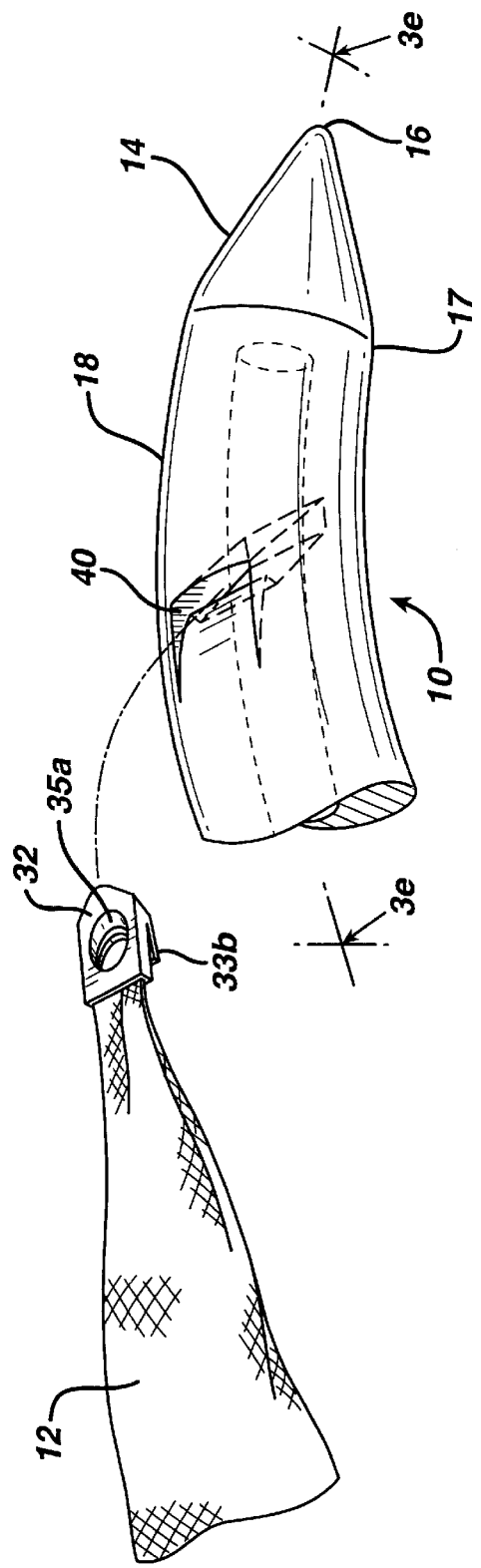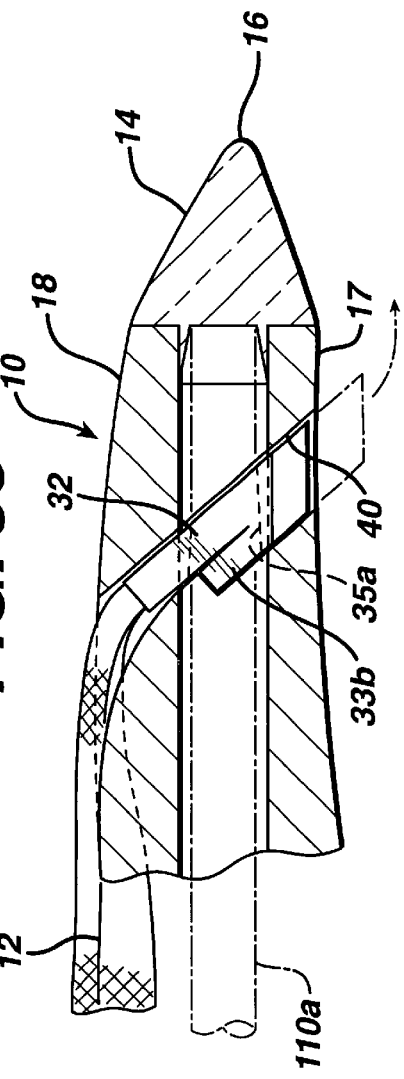

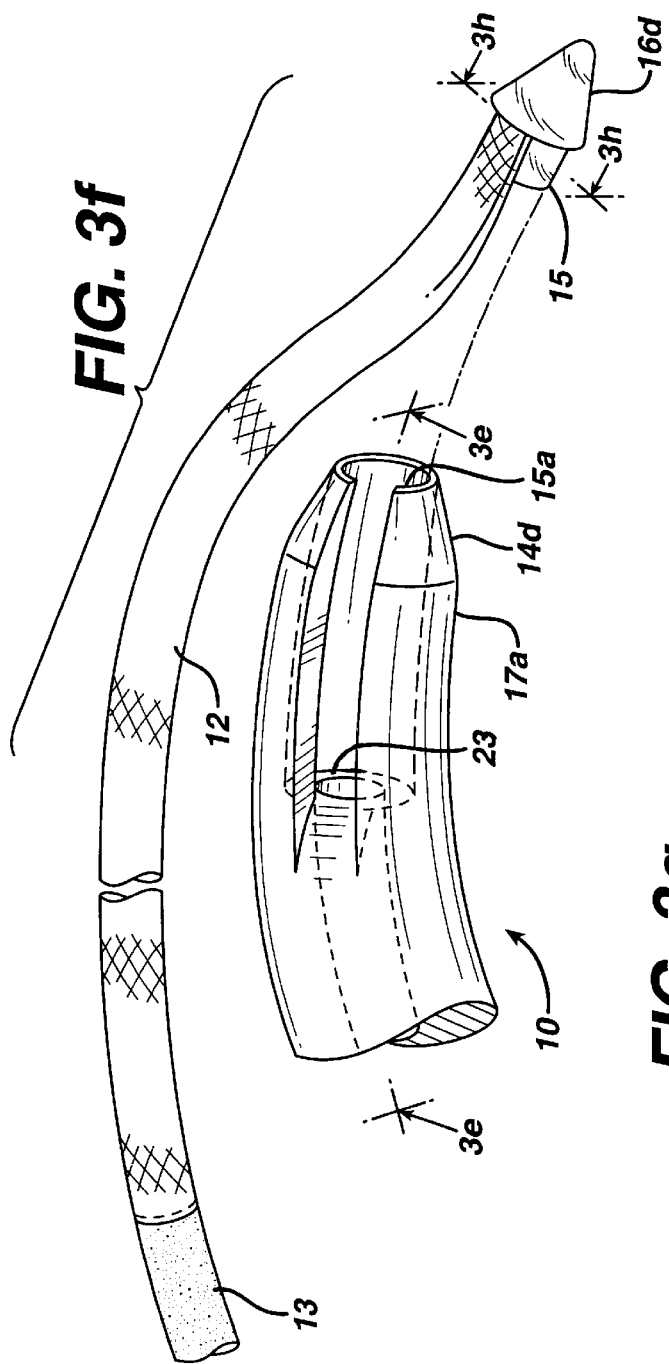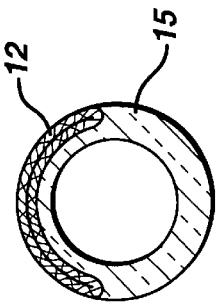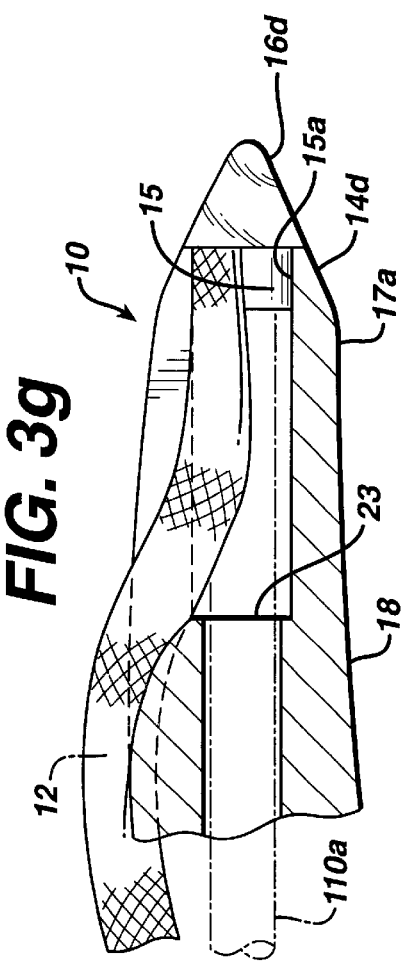

VISUALLY-DIRECTED SURGICAL INSTRUMENT AND METHOD FOR TREATING FEMALE URINARY INCONTINENCE

CROSS REFERENCE TO RELATED APPLICATION

The present invention claims the benefit of earlier-filed United States provisional patent application, Ser. No. 60/138,231, filed on Jun. 9, 1999, which is hereby incorporated by reference in its entirety herein.

BACKGROUND OF THE INVENTION

The present invention relates generally to a surgical instrument and a method for treating female urinary incontinence and in particular to a needle adapted to provide visualization of the tissue during the procedure.

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, adjusting the loop to bring the vaginal wall and the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one end of a tape intended to be implanted into the body. In practice, the tape is passed into the body via the vagina first at one end and then at the other end at one side and the other, respectively, of the urethra to form a loop around the urethra, located between the urethra and vaginal wall. The tape is extended over the pubis and through the abdominal wall and is tightened. The tape ends are cut at the abdominal wall, and the tape is left implanted in the body. U.S. Pat. No. 5,899,909 is incorporated herein by reference.

One particular disadvantage of the prior art, especially for surgeons unfamiliar with the surgical method is not completely knowing the location of the needle tip relative to adjacent pelvic anatomy. If the needle tip is allowed to accidentally pass across the surface of any blood vessel, lymphatic duct, nerve, nerve bundle or organ possible complications may arise.

It would be beneficial to provide a needle for use in implanting a mesh tape within a female body to prevent incontinence that has a design that provides for visualization of the tissue as the needle passes through the woman's lower abdomen.

SUMMARY OF THE INVENTION

The invention overcomes the deficiencies of the prior art and provides for an improved needle for use with an apparatus and a method for the treatment of female stress urinary incontinence. The invention provides a surgical instrument comprising a handle at one end and connecting means at the other end to receive, one at a time, two curved needle-like elements, each of which has a modified tip. The needle may have a constant or varying diameter. Each needle connects at one end to separate ends of a tape intended to be implanted within the body. In practice, a first end of the tape is passed, via one of the curved needles, into the body via the vagina at one side of the urethra. The needle and first end of the tape pass over the pubis and through the abdominal wall. The second needle element connects to the second end of the tape and passes into the body via the vagina at the opposite site of the urethra from the first end of the tape thereby forming a loop or sling around the urethra with the tape. The second end of the tape is extended over the pubis and through the abdominal wall. The tape ends are cut at the abdominal wall, and the tape is left in the body.

The invention further provides for a single curved needle element having a modified tip. The needle may have a constant or varying diameter and further provides for a easy attachment means enabling the surgeon to connect both the first and second tape ends to the single needle to perform the above-stated procedure.

In both embodiments, the needle is modified to contain an inner lumen for passage of optical devices and/or fluids. A surgical optical system may interface directly with the needle, or alternatively, the hand piece or handle may be modified to accept the optical system. The tip of the needle is also modified to contain a window or viewing port that allows for the transmission of light from the ambient target tissue into the imaging lens of the optical system. The optical system allows the surgeon to maintain continuous anatomic visualization during introduction and navigation of the needle within the lower abdomen.

The object of the invention is to provide a surgical instrument for implanting a mesh to treat incontinence that provides for an optical viewing system that allows the surgeon to view tissue and vital organs as the needle penetrates the lower abdomen of a female patient.

An advantage of the invention is that it reduces the risk of perforating unintended body structures when carrying out the procedure.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3a–h embodiments of means for attaching the tape to the needle;

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

The invention discloses an apparatus and method for treating SUI. A tape is passed through pelvic tissue and positioned underneath the urethra, creating a supportive sling. The tape provides a structure means for tissue ingrowth and thereby provides a newly created body tissue supporting means for the urethra. When pressure is exerted upon the lower abdomen, such as during a cough or sneeze, the tape provides support to the urethra, allowing it to keep its seal and prevent the unwanted discharge of urine.

Figure 1A:
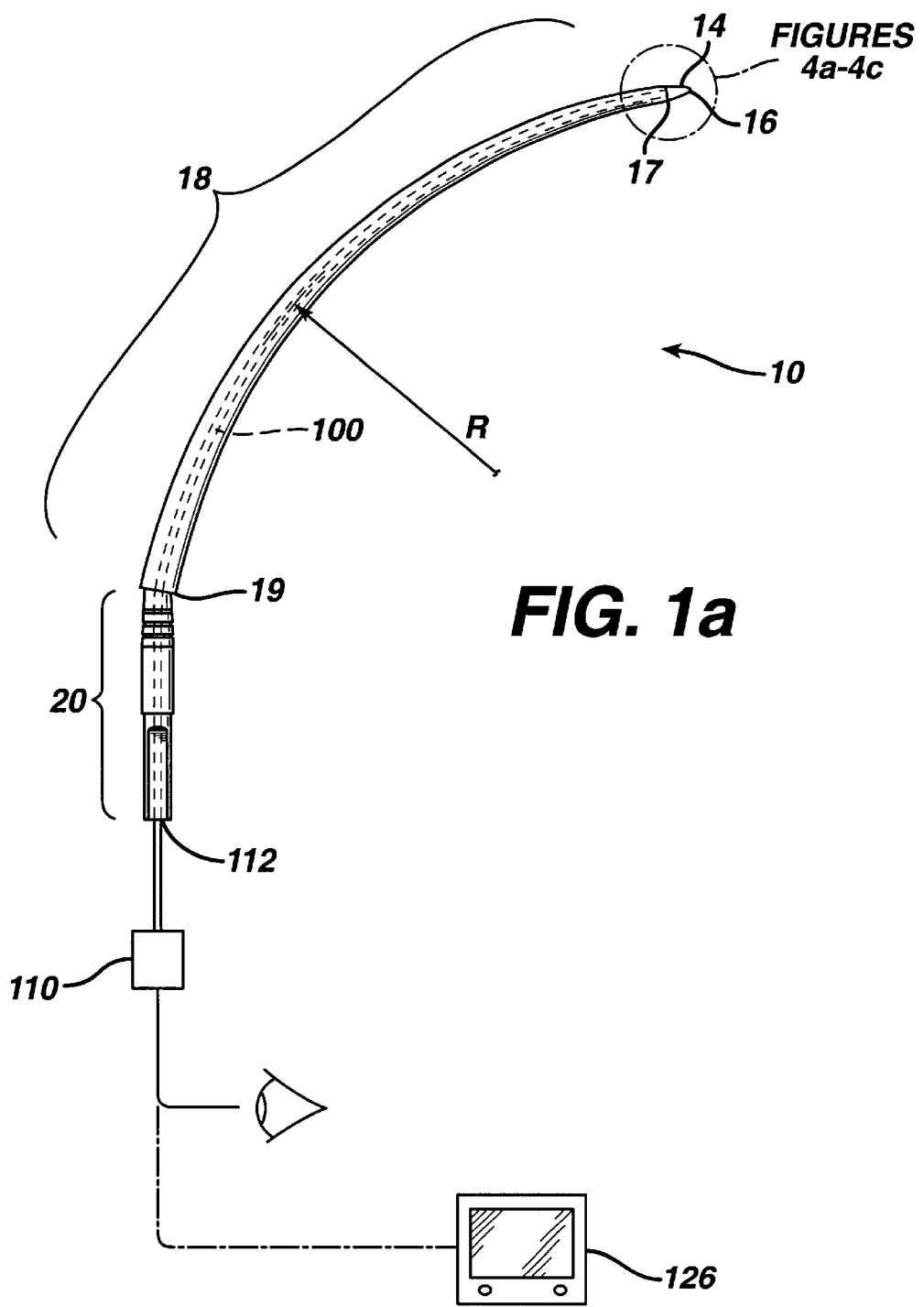
FIG. 1a is a view of the needle in one embodiment thereof.
Figure 2A:
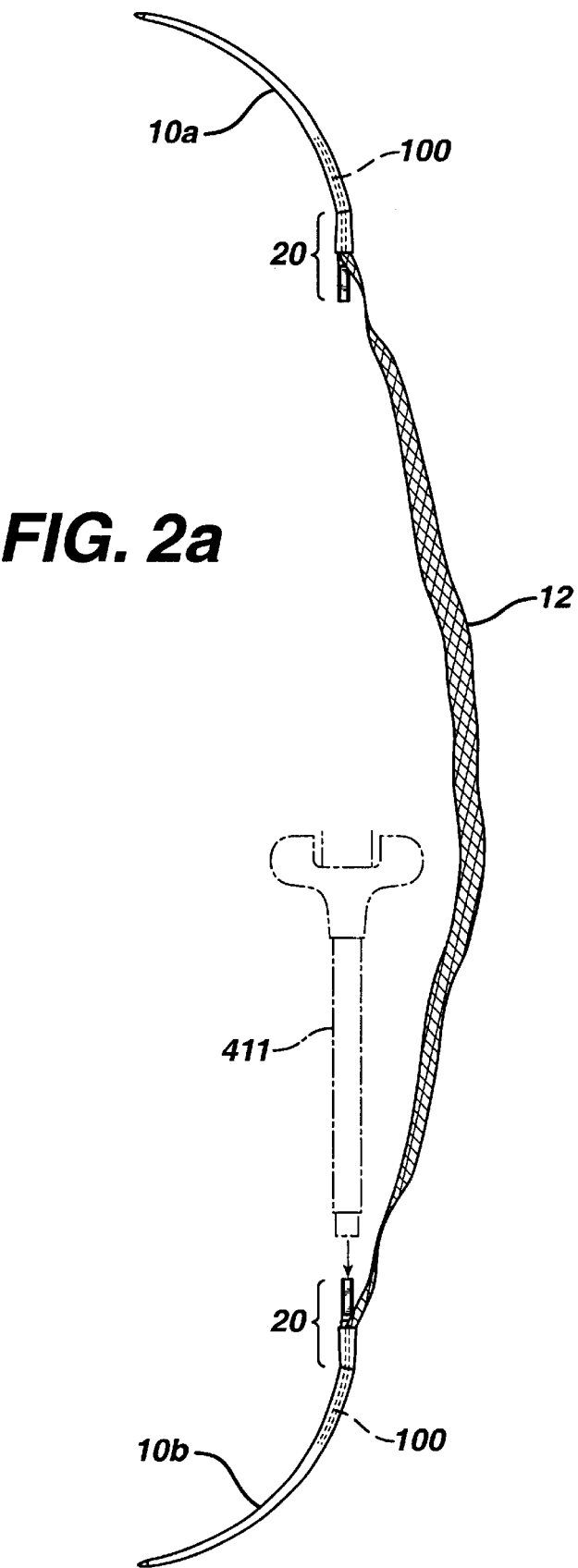
FIG. 2a is a side view of two needles and a tape interconnecting the needles.

Referring to FIGS. 1a and 2a, the surgical instrument comprises a needle-like element 10 that attaches to a mesh tape 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the tape as described below. In one embodiment, blunt tip 16 is made from a clear material, having good optical properties that allows for radial viewing of the tip proximity over a prescribed depth of field. Blunt tip 16 may be manufactured from a clear polymer or glass.

The proximal end of needle 10 terminates in an attachment segment 20 that is adapted to mate and lock into a handle 411 as disclosed in U.S. Pat. No. 5,899,909, previously incorporated herein by reference.

Disposed between cone portion 14 and segment 20 is a curved shaft 5 segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of the curved shaft segment 18 may be constant or the diameter of segment 18 transitions from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm. Preferably, the diameter at the proximal end is about 6 mm, and reduces in a continuous manner to a diameter of about 3 mm at the distal end 17. This design takes into account, that in the method to implant the tape 12, the bending stresses are lowest at distal end 17, while the bending stresses are highest at the proximal end 19. Stated differently, during the procedure, the inner bending moment at distal end 17 is negligible, while the inner bending moment at the proximal end 19 is substantial.

Segment 20, curved segment 18 and cone portion 14 are further modified to include a lumen 100 for accepting a light and/or imaging system of an optical system. The optical system includes a flexible or semi-rigid endoscope 110, which has the flexing capability to follow the curvature of needle 10. Preferably, the endoscope comprises a fiber bundle of less than 40K, and more preferably, the scope has a fiber bundle of 30K to allow the scope to bend along the radius of needle 10. As illustrated the lumen 100 is located concentrically through needle 10 and access port 112 is located at the proximal end of portion 20. This embodiment allows the entire needle 10 to be placed in-vivo before requiring the removal of the scope 110 from lumen 100 as discussed below. The surgeon may view the procedure through the eyepiece of the endoscope 110. Alternatively, the surgeon may view the procedure via a viewing screen 126 in combination with camera head mounted to the eyepiece of the endoscope. Such optical systems are well known to those skilled in the art.

Lumen 100 may also serve as a conduit for passing fluids through needle 10. For example, an irrigation solution may be passed through needle 10 and through cone portion 14 to clear the field of view at cone portion 14. Additionally, water flow via lumen 100 may be used to produce a passageway through the tissue for needle 10 via hydrojetting. Lumen 10 may also be used to deliver a radiopaque fluid for fluoroscopic examination or to deliver drug therapy. Alternatively, a fluid delivery lumen could be separate and parallel to lumen 100. The fluid delivery lumen could exit cone portion 14 or it could exit needle 10 immediately adjacent and proximal to cone portion 14.

Figure 1B:
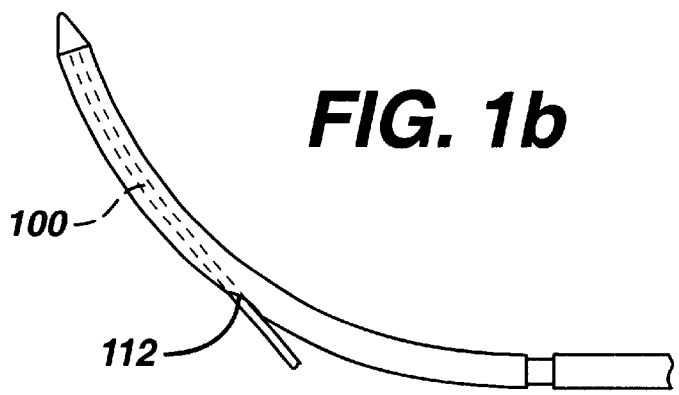
FIGS. 1b–d are views of alternate embodiments of the needle.
Figure 1C:
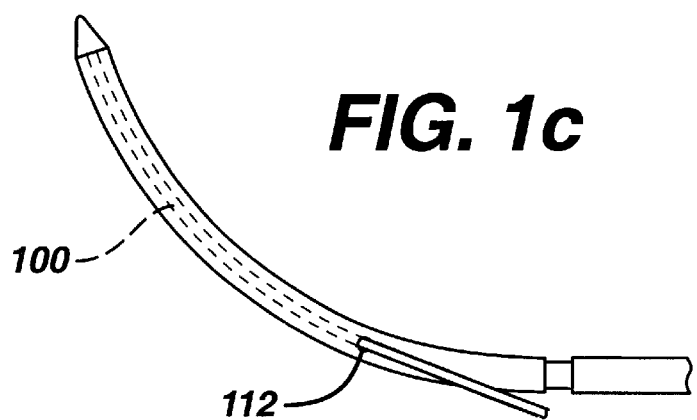
Figure 1D:
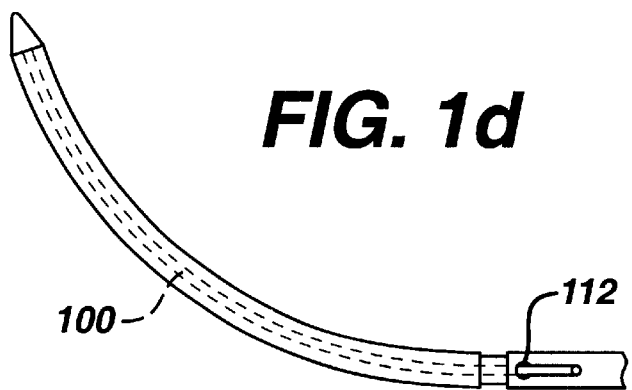

Lumen access port 112 may be located at the outer arcuate portion of curved segment 18 as shown in FIG. 1b; lumen access port 112 may also be located to allow lateral (left or right) entry and exit of endoscope 110 to needle 10, FIG. 1c; or as shown in FIG. 1d, lumen access port 112 may be located adjacent to the hand piece connection allowing all of the needle to be place in-vivo before having to remove endoscope without requiring modification of the handle as discussed below.

Figure 4A:
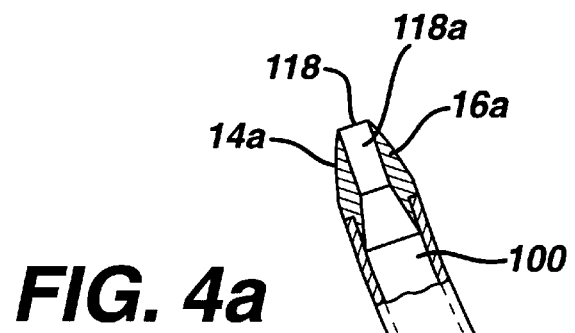
FIGS. 4a–c are embodiments of the viewing ports at the tip of the needle.
Figure 4B:
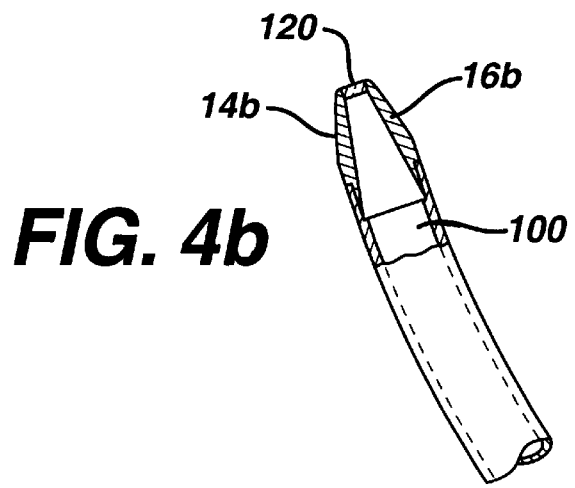
Figure 4C:
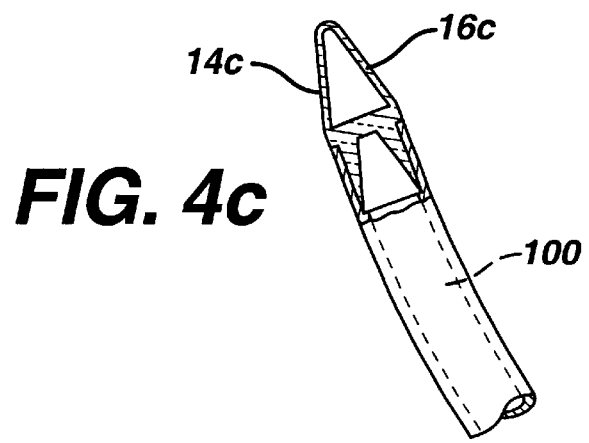

Alternate embodiments of cone portion 14 are disclosed in FIGS. 4a–c. FIG. 4a illustrates cone portion 14a comprising an open port 118 at the distal end of tip 16a. Lumen 118a allows the endoscope to pass through the cone portion 14 for tissue inspection prior to needle advancement. FIG. 4b discloses a cone portion 14b with the distal end terminating at a glass window/lens port 120. Alternatively, cone portion 14c may be made from clear polymer or glass to allow for radial viewing of the tip proximity over a prescribed depth of field as shown in FIG. 4c.

Figure 5:
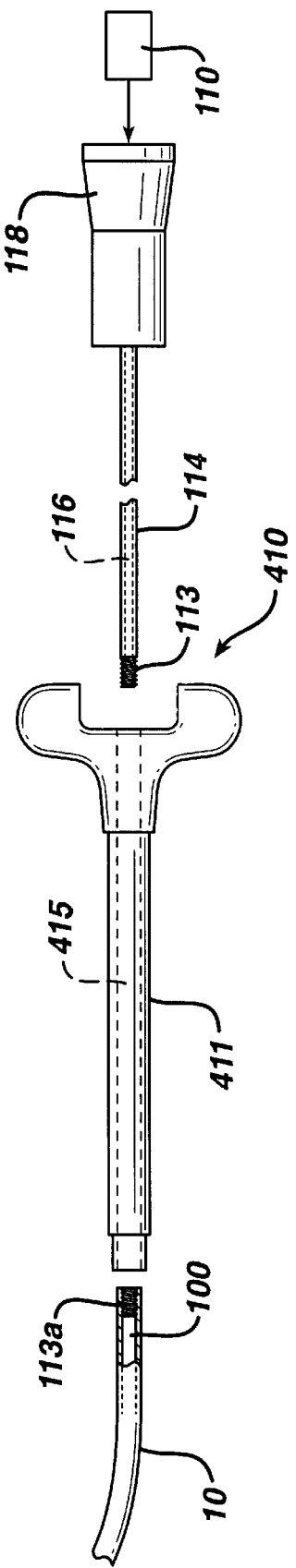
FIG. 5 is an assembly schematic of the needle and handle.

In the embodiment disclosed in FIG. 5, the prior art handle and rotating cylindrical shaft, as disclosed in U.S. Pat. No. 5,889,909 are modified to accept an endoscope. As shown in FIG. 5, the handle 411 of the prior art is modified to include an open grip 410. Shaft 415 receives a threaded tip 113 of a fastening rod 114 having an internal lumen 116 and an integrated optical scope docking hub 118 for receiving an endoscope. Threaded tip 113 threadably affixes to the threaded section 113a at the proximal end of needle 10 as discussed in U.S. Pat. No. 5,889,909. Once fastening rod is securely fixed to needle 10, endoscope 110 may be inserted through shaft 415 and central lumen 100 of needle 10 until endoscope terminates at cone portion 14.

Needle 10 is preferably tubular with a circular cross section and is made from a material that is compatible with the human body. It is also preferred that needle 10 is made from a material that can be autoclaved to enable multiple surgical procedures of needle 10. Preferably, needle 10 is made from 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the tape 12.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
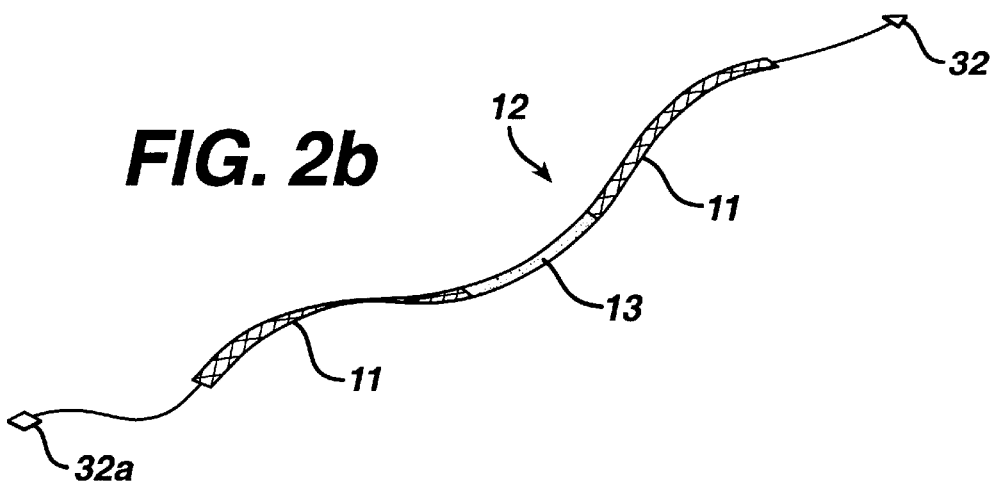
FIGS. 2b–d are alternate embodiments of the tape and connecting means a between the tape and needle.
Figure 2C:
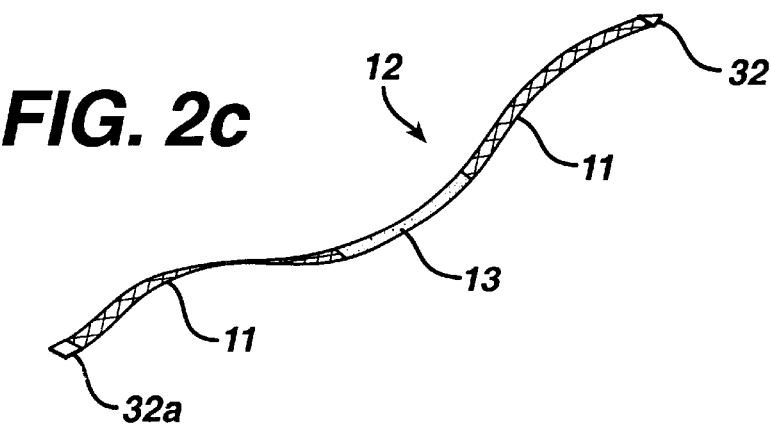

Referring to FIGS. 2a–d, tape 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the tape 12 is a combination of a synthetic material 11 and a natural material 13 centered between the synthetic material 11 as shown in FIGS. 2b–c. A still further embodiment of the tape 12 includes a combination of synthetic material 11 and natural material 13, whereby the natural material is placed over or incorporated within a generally central portion of the synthetic material 11. One advantage of the tape configurations is that natural material 13 is along the center region of tape 12 so that after installation of tape 12, natural material 13 is positioned below the urethra and eliminates possible erosion issues at the interface of the urethra and tape. Natural material 13 may be connected to the synthetic material 11 by means of sewing, a bio-compatible glue, cell culturing techniques or other known means.

Tape 12 may be of any convenient shape that suits the intended purpose of the invention. An exemplary width is about 1 cm and the length would be dependent upon the size of the female undergoing the procedure. Tape 12 may be single or double ply, generally planar in structure, or tubular (FIG. 2d) to provide additional supporting strength and more surface area on which tissue fibers may attach. Moreover, tape 12 may consist of different types of material, such as a bioabsorbable and non-bioabsorbable material. Tape 12 may also be coated with an antimicrobial additive to prevent or minimize infection and a lubricous coating, for example, a bioabsorbable hydrogel, to facilitate the tape passing through the tissue as discussed below. Preferably, tape 12 is covered by a removal plastic sheath as disclosed in U.S. Pat. No. 5,899,909. The tape may also be made radio-opaque and/or of a contrasting color to the body tissue to allow for future diagnostic visualization.

In one embodiment tape 12 may be attached to needle segment 20 by means of tying, gluing or other suitable attaching means. Preferably, a bi-compatible heat shrink tube fixes tape 12 onto needle portion 20, FIG. 2a. In a further embodiment, as shown in FIGS. 2b–d and 3a–h, needle 10 and tape 12 are further configured to enable easy attachment and detachment of tape 12 to and from needle 10 by the surgeon during the operation. This embodiment allows for the use of a single needle for the procedure. This embodiment also allows for the use of a tape constructed, at least in part, of natural materials, which are otherwise not suitable in the pre-affixed embodiment due to the inability of the natural material to survive extended periods in inventory.

Figure 2D:
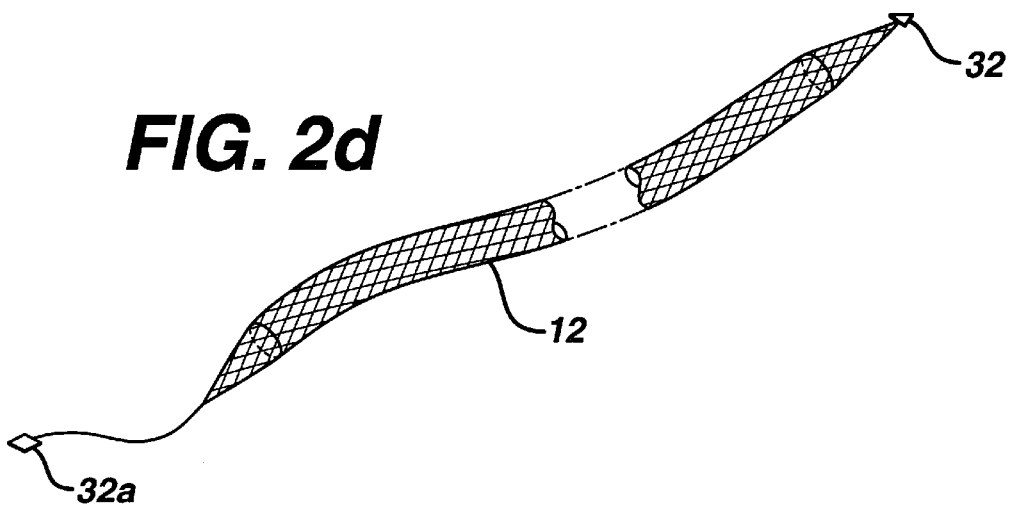
Figure 3A:
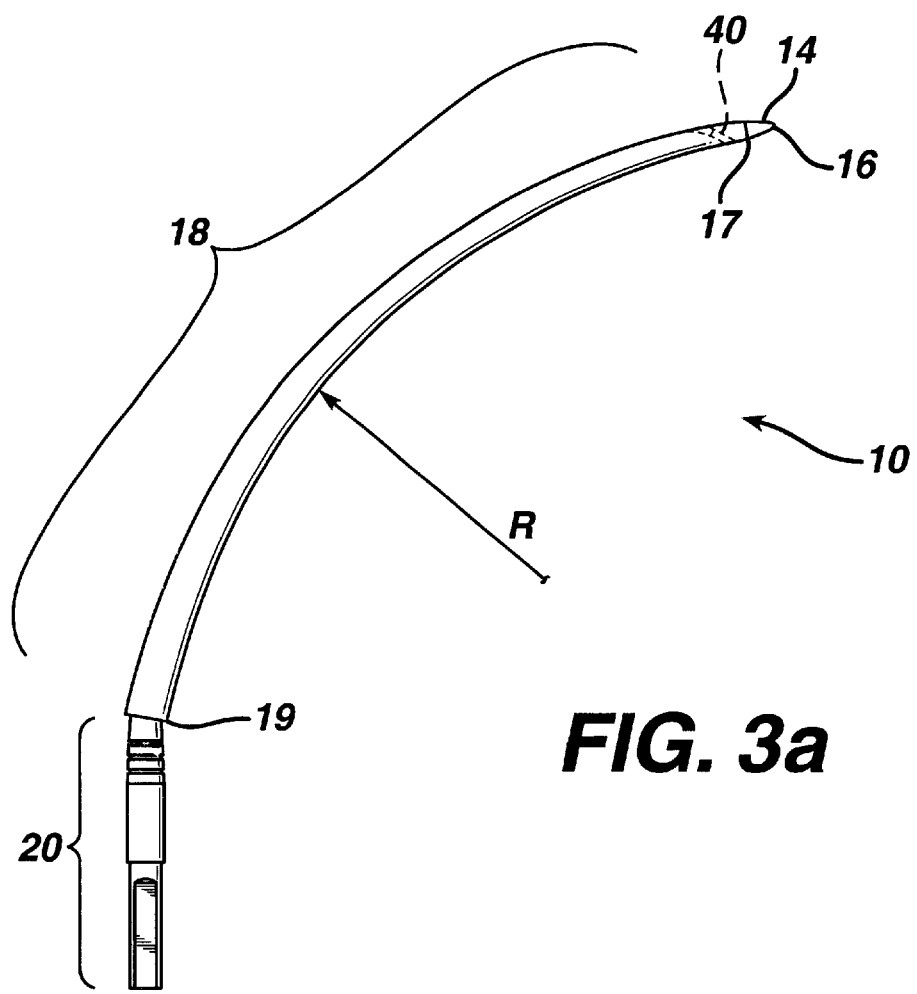

In one embodiment, shown in FIGS. 3a–c, shaft 18 provides for a notch or slot 40 to slidably receive connecting tabs 32 and 32a that are attached at either ends of tape 12 (see FIGS. 2b–d). Preferably, slot 40 extends through curved shaft 18 and is further located at the distal end 17 of needle 10 so that tape 12 may be disconnected from needle 10 immediately after needle 10 penetrates the abdomen wall, discussed below.

Tab 32 may be constructed from any bio-compatible material, such as plastic or metal. Tab 32 can be any shape, such as a square or arrow shape, so long as tap 32 can be securely inserted into notch or slot 40. FIG. 3b–c illustrates tab 32 having two spring arms 33 and 33a that when inserted into slot 40 expand and securely fasten tab 32 within slot 40. Tab 32 may be attached to tape 12 in any number of convenient methods as previously discussed and well known to those skilled in the art. Tab 32 is further configured to include an opening 35, which permits the imaging fibers 110a of endoscope 110 to pass through to cone tip 14.

FIG. 3d–e illustrates a two-tier slot 40, wherein tab 32 and spring element 33b slide into the lower tier which holds tab 32 in place. Tab 32 is further modified to include opening 35a to permit the imaging fibers to pass through to cone tip 14. Alternate means of capturing tab 32 within slot 40 are available as is well known in the art.

FIGS. 3f–h illustrate an alternate embodiment of affixing tape 12 to the distal end 17a of needle 10. A detachable blunt tip 16d having a connecting post 15, attaches to the distal end 17a by means of a mounting hole 15a to accept post 15. Post 15 may be securely attached to hole 15a either by compression fit, mating threads or other convenient attachment methods. Post 15 also includes a lumen to allow the imaging fibers to pass to the distal end of cone tip 14d. Further, as shown in FIG. 3h, tape 12 is attached to the outer circumference of post 15 to allow for the imaging fibers to pass through. Distal end 17a further defines a groove 23 of varying depth to allow the end of tape 12 connected to post 15 to transition from within hole 15a to the exterior of needle 10. Along with the embodiment of FIGS. 3a–e, this embodiment allows the surgeon to affix tape 12 to needle 10 just prior to the surgical procedure. One advantage is the ability to use a tape 12 constructed of, at least in part, a natural material 13.

As would be appreciated by one skilled in the art, there exist multiple means for detachably connecting the tape to the needle. Alternate embodiments would include tying the ends of tape 12 to form a knot and securely inserting the knot into a V-type groove in shaft 18. Alternately, a diagonal slit in shaft 18 could accept tape 12 or a suture extending from tape 12.

The surgical procedure for implanting tape 12 using two needles is shown in FIGS. 6a–g utilizing the needle embodiment illustrated in FIGS. 1a and 2a. In the figures the relevant parts of the female lower abdomen are disclosed, the vagina being 50, the uterus 52, the urethra 54, the pubic bone 56, the urinary bladder 58 or and the abdominal wall 60. The first needle 10a penetrates the vaginal wall, an incision having first been made in the wall to create a tissue flap. The needle is attached to handle 411, and an endoscope is inserted through lumens 116 and 100 until the scope terminates at the distal cone portion 14 of needle 10a. While viewing the visual feedback of the endoscope, preferably on an overhead screen 126, the surgeon guides needle 10a through the vaginal wall and through the soft tissue on one side of the urethra 54, the needle then according to FIG. 6b being passed close to the back of the pubic bone 56, through additional layers of fat, muscle and fascia, and then through the abdominal wall 60 above the pubic bone 56. An incision can be made through the abdominal wall for the passage of the needle therethrough. The endoscope is removed from within lumen 100, and handle 411 is disconnected from needle 10a, FIG. 6c, and the needle 10a along with tape 12 are withdrawn from the abdominal wall by means of forceps, FIG. 6d.

Figure 6A:
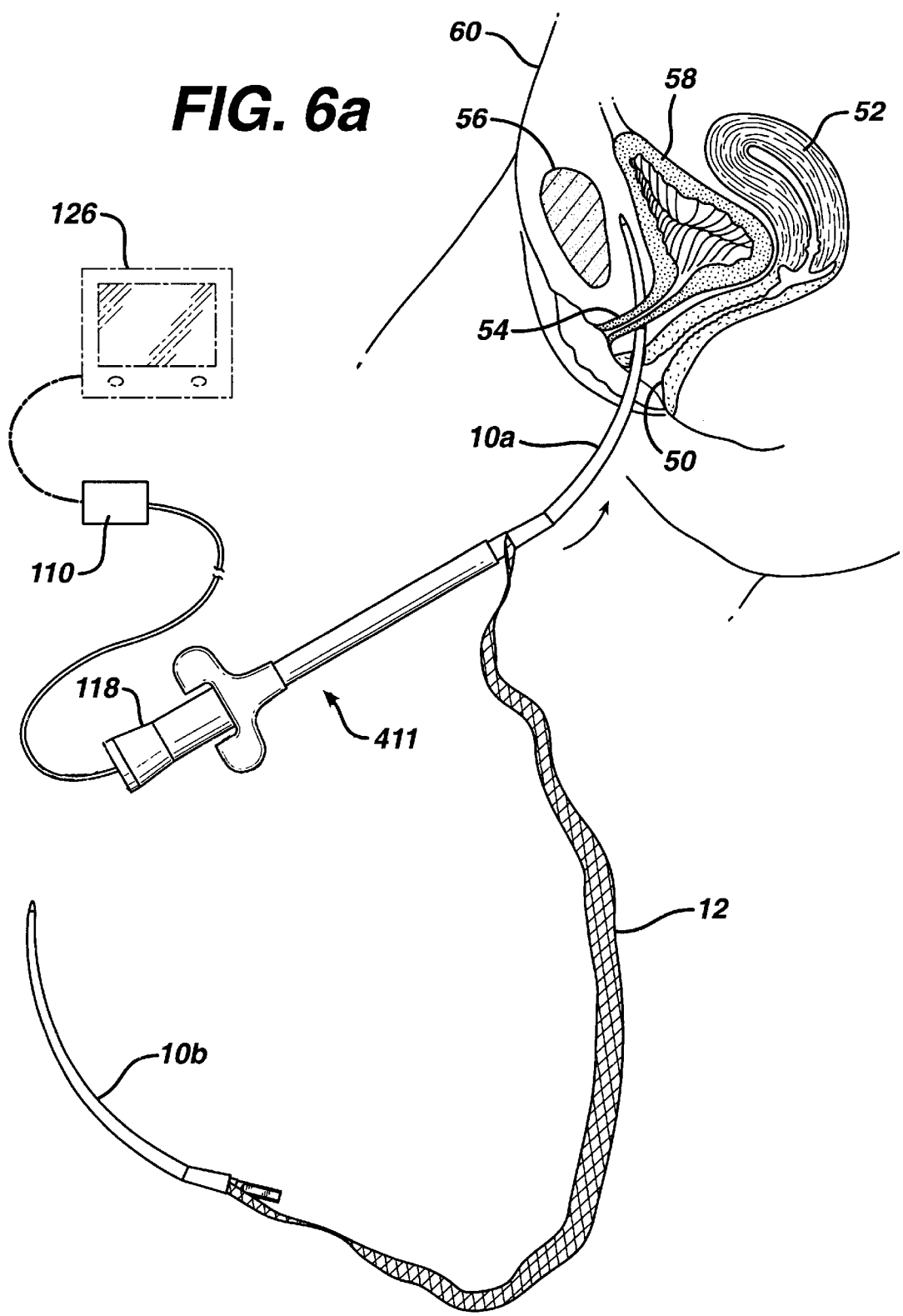
FIGS. 6a–g illustrate diagrammatically several surgical steps of the method utilizing two needles according to the invention to treat SUI.
Figure 6B:
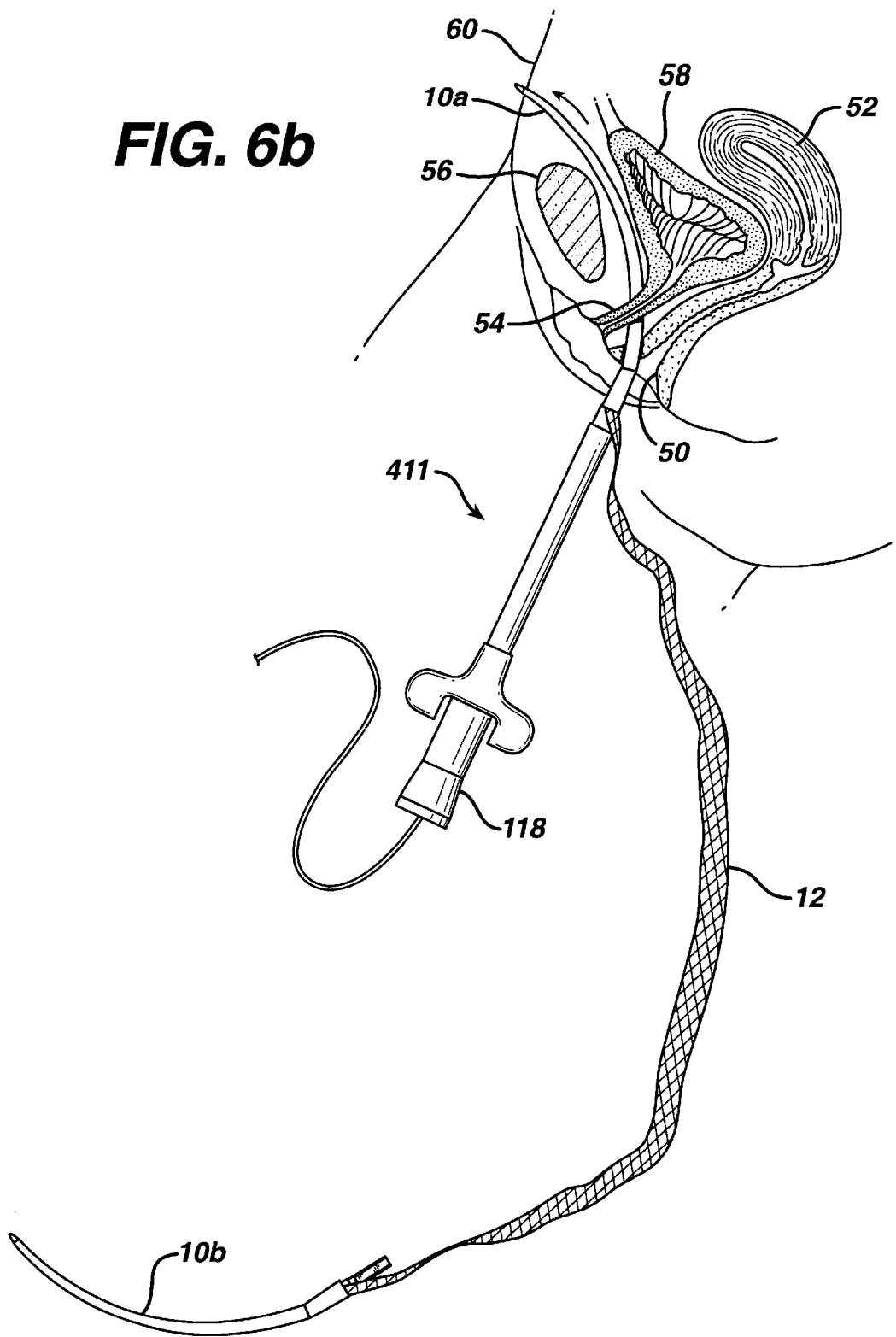
Figure 6C:
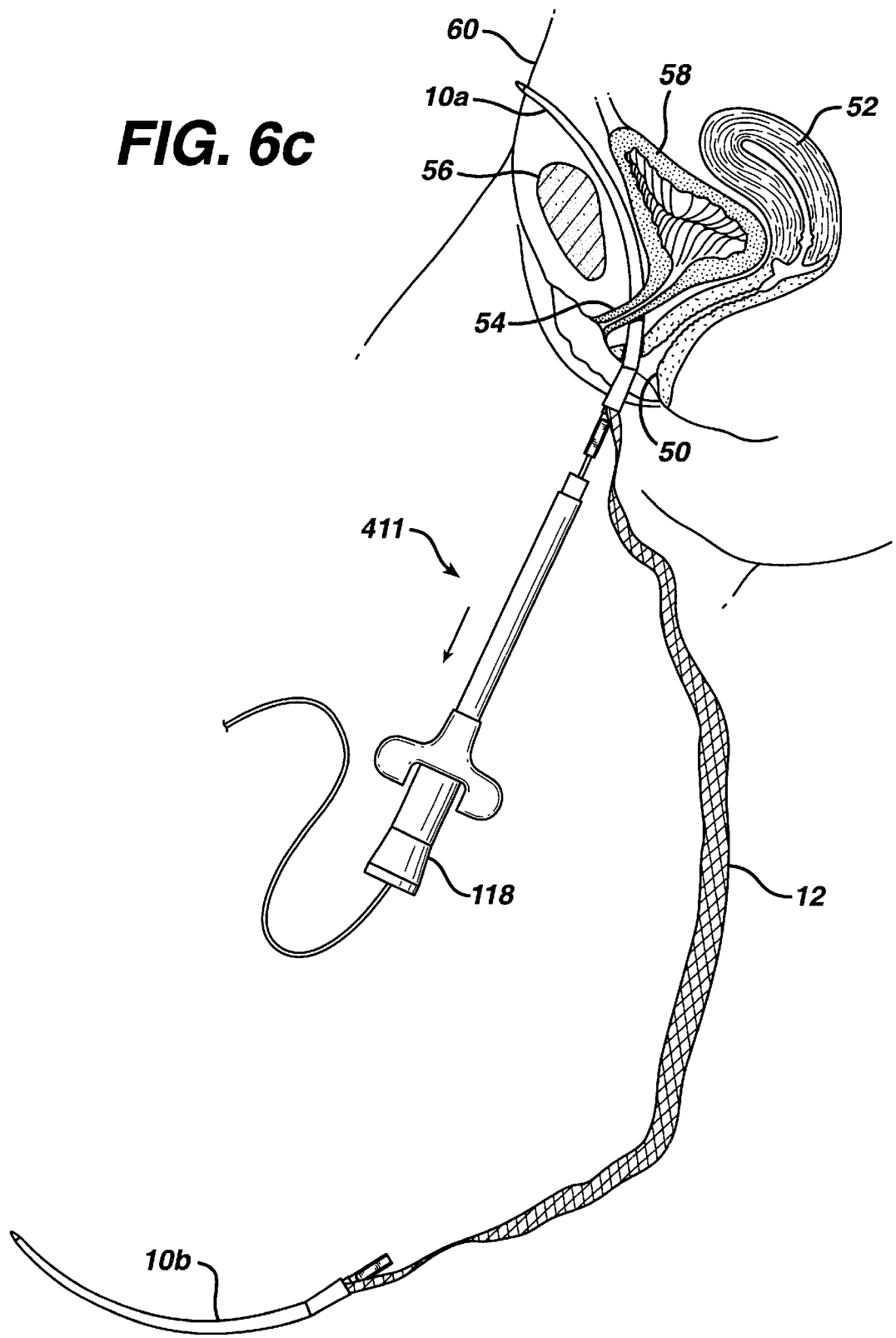
Figure 6D:
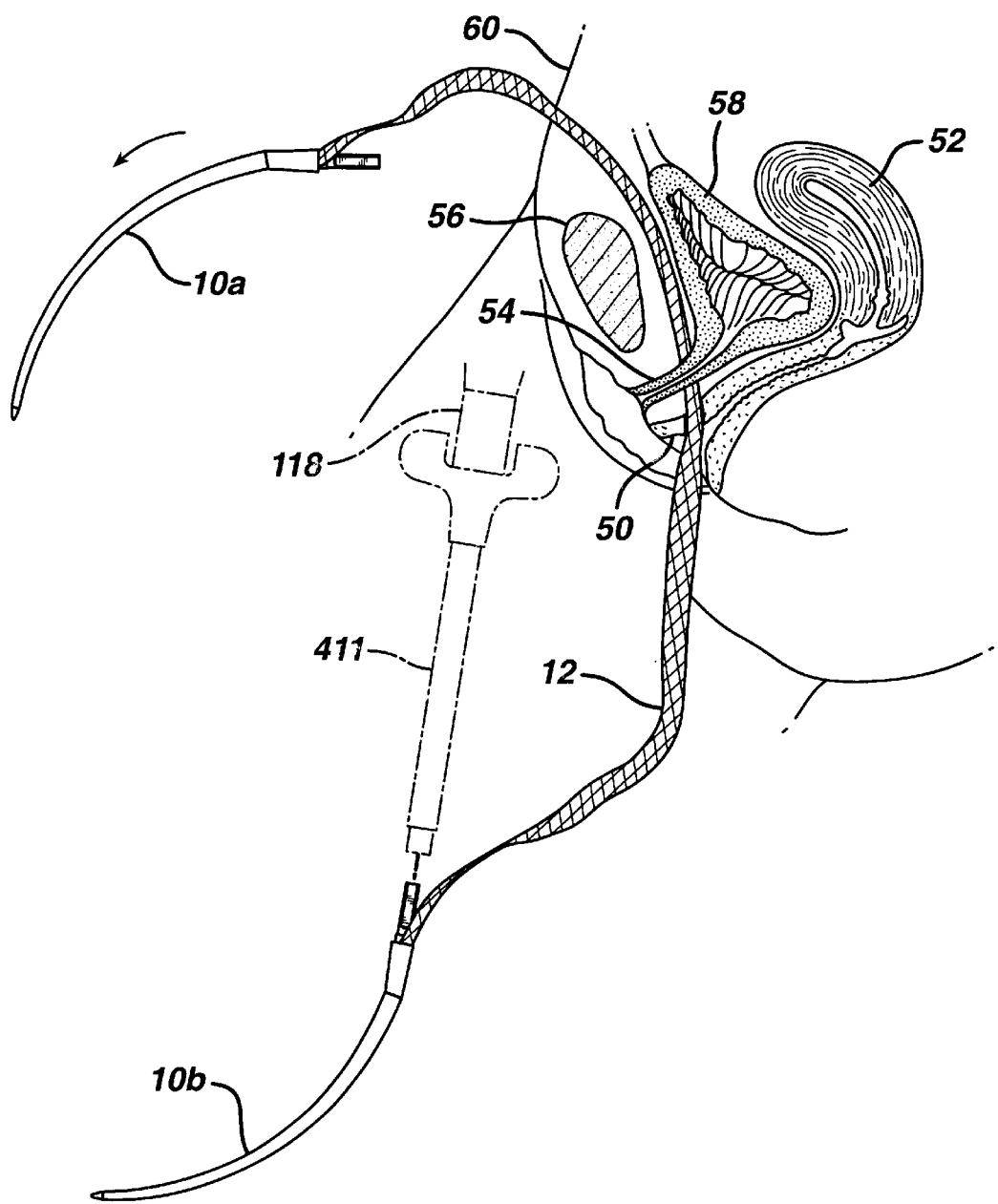
Figure 6E:
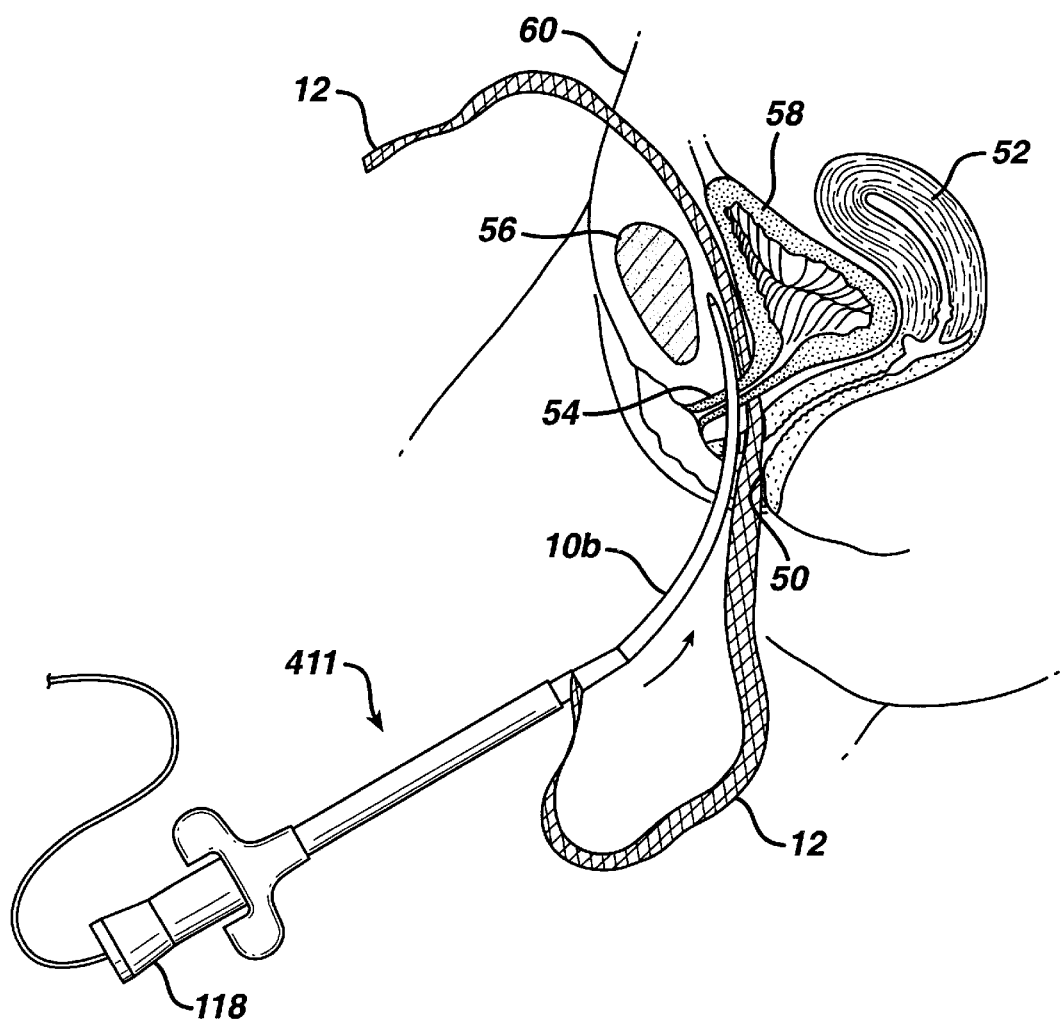
Figure 6F:
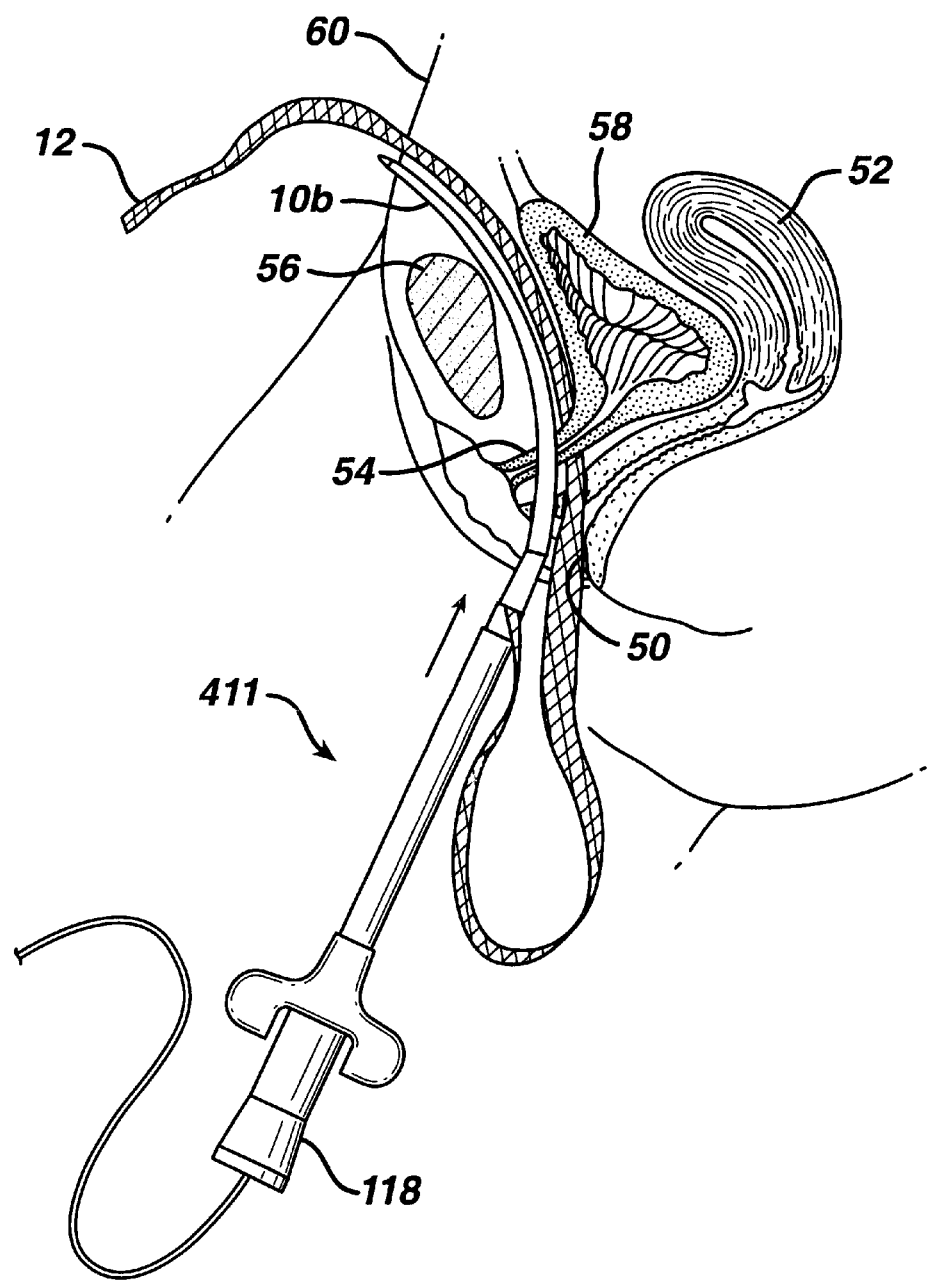
Figure 6G:
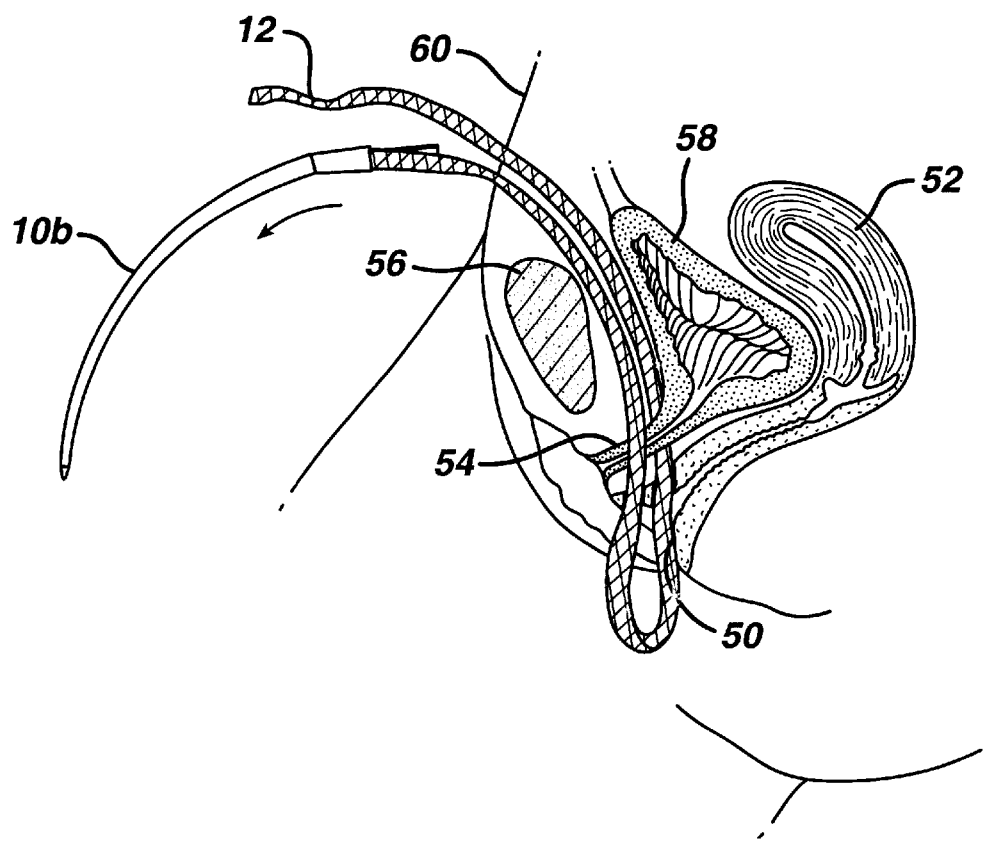

Referring to FIG. 6e, needle 10b is now attached to handle 411 and endoscope 110. The surgeon passes needle 10b through the incision in the vaginal wall and through the soft tissue, again, while viewing the image from the endoscope 110, on the opposite side of the urethra than the previous end of tape 12. Needle 10b passes close to the back of the pubic bone, through additional layers of fat, muscle and fascia, FIG. 6f, and then through the abdominal wall above the pubic bone and withdrawn, FIG. 6g.

FIGS. 7a–g illustrate an alternate method of implanting tape 12 using a single needle 10. Tape 12 is attached to needle 10 by means of conical portion 14 as shown in FIG. 3f. Needle 10 penetrates the vaginal wall, an incision having first been made in the wall to create a tissue flap. While viewing the visual feedback of the endoscope 110, preferably on an overhead screen 126, the surgeon guides needle 10 through the vaginal wall and through the soft tissue on one side of the urethra 54, the needle then according to FIG. 7b being passed close to the back of the pubic bone 56, through additional layers of fat, muscle and fascia, and then through the abdominal wall 60 above the pubic bone 56. An incision can be made through the abdominal wall for the passage of the distal end 17 therethrough. Needle 10 only continues to pass through the abdominal wall until cone portion 14 may be disconnected from needle 10, FIG. 7c. To do so, the surgeon simply pulls off cone portion 14 using forceps. Cone portion 14 may then be cut off and tape 12 may be pulled out of the abdominal wall to allow the surgeon additional length for the procedure. Needle 10 is then removed from the patient along the same path that it entered, but in the opposite direction, FIG. 7d. Alternatively, needle 10 may be disconnected from handle 411 and endoscope 110 and pulled out through the abdomen wall 60 using forceps as discussed with regard to the two needle procedure.

Needle 10 is now attached to the opposite end of tape 12 using connector cone portion 14. The surgeon passes needle 10 through the incision in the vaginal wall and through the soft tissue on the opposite side of the urethra than the previous end of tape 12, FIG. 7e. Needle 10 passes close to the back of the pubic bone, through additional layers of fat, muscle and fascia, FIG. 7f, and then through the abdominal wall above the pubic bone. Needle 10 continues to pass through the abdominal wall only until cone portion 14 may be disconnected from needle 10, FIG. 7g. Tape 12 may be pulled out of the abdominal wall to allow the surgeon additional length for the procedure. Needle 10 is then removed from the patient along the same path that it entered, but in the opposite direction. Alternatively, needle 10 may be disconnected from handle 411 and pulled out through the abdomen wall 60 using forceps.

Figure 6H:
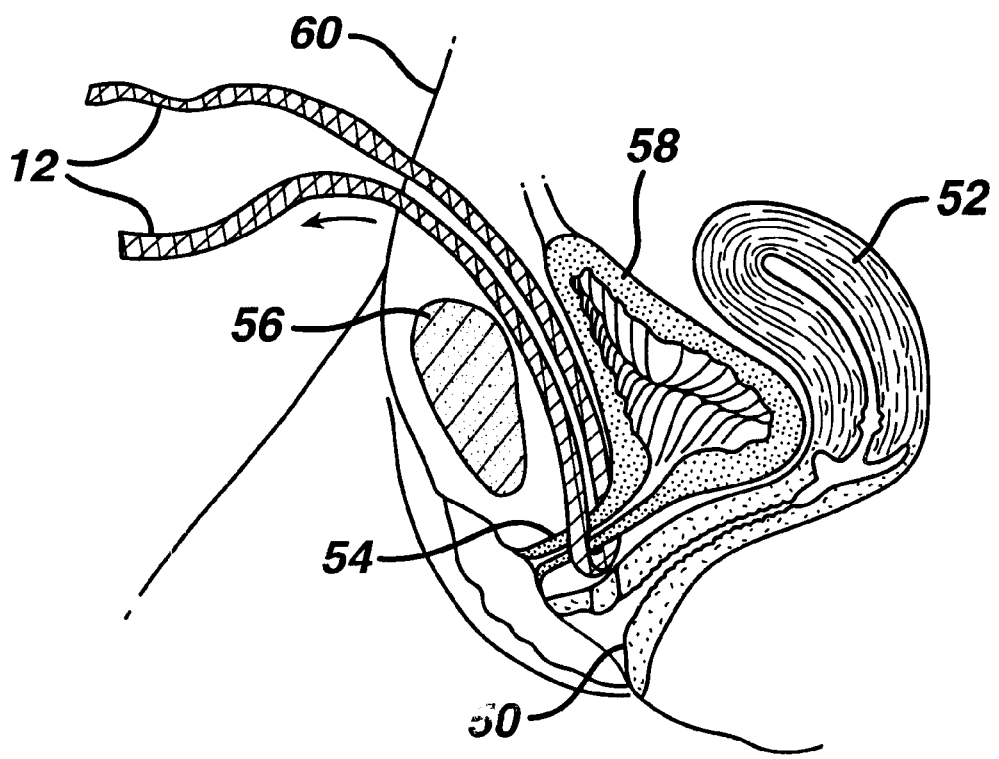
FIG. 6h illustrates the final position of the tape within the body before the tape ends are cut.
Figure 7A:
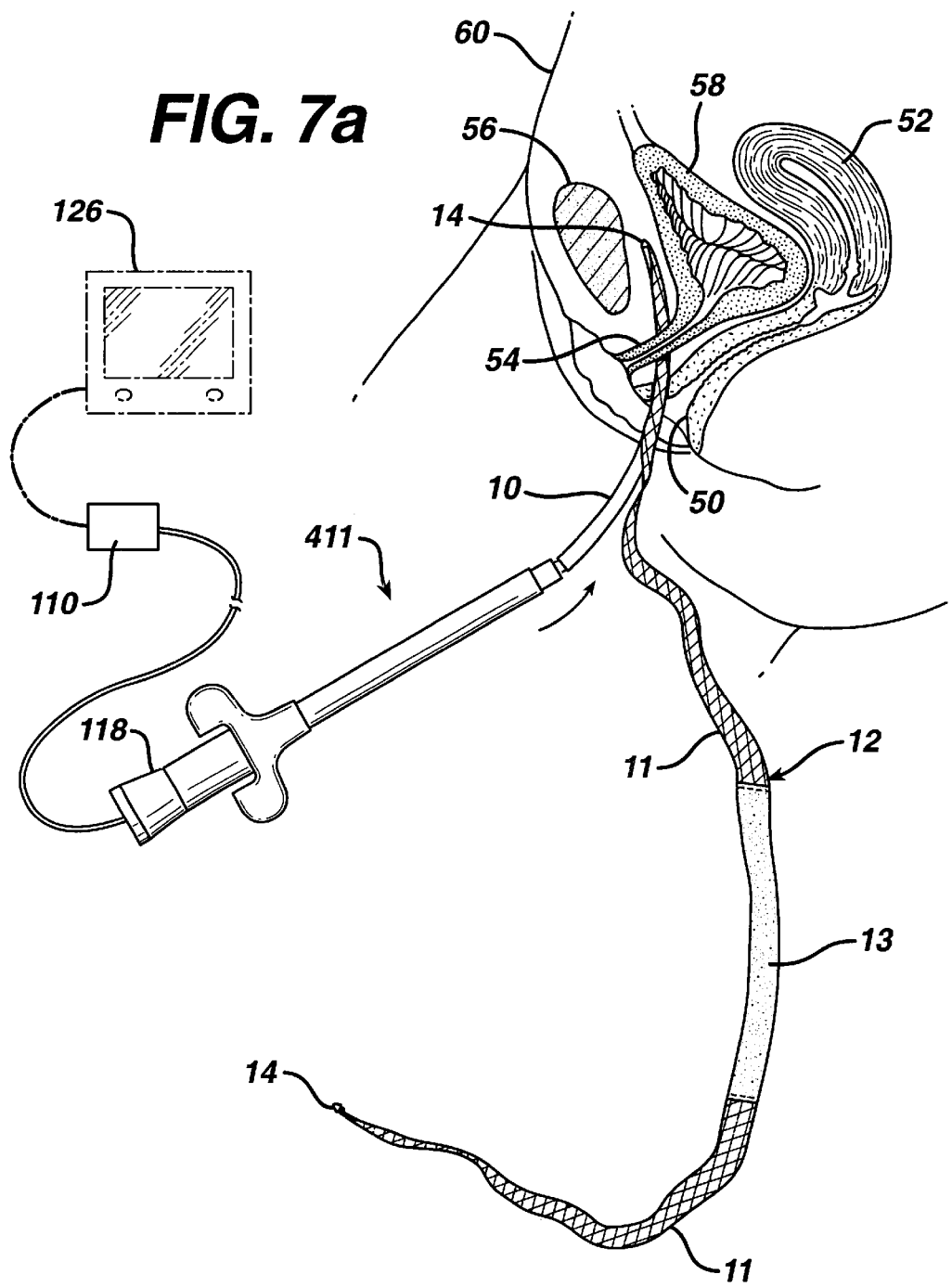
FIGS. 7a–h illustrate diagrammatically surgical steps of the method utilizing one needle according to the invention to treat SUI.
Figure 7B:
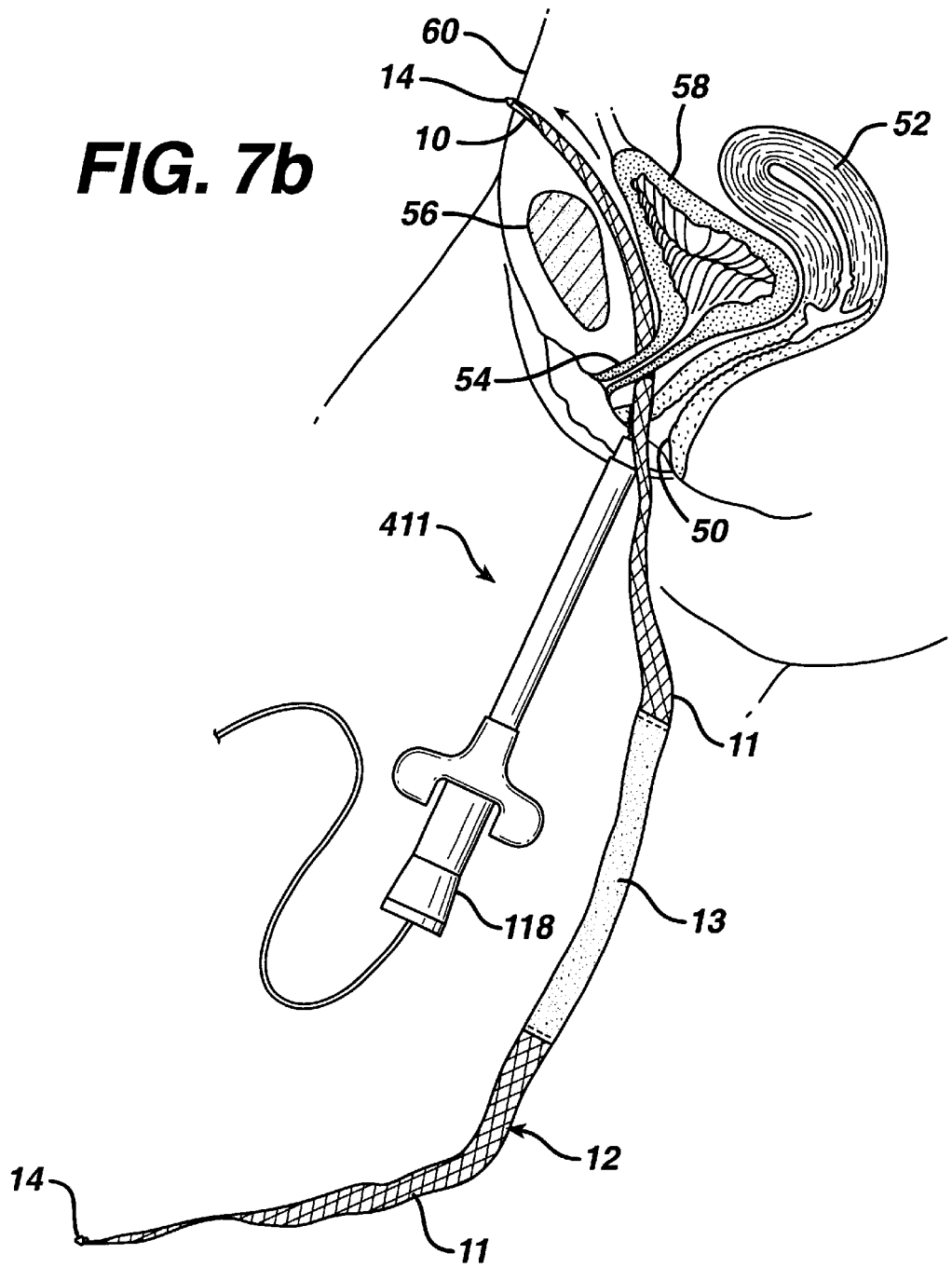
Figure 7C:
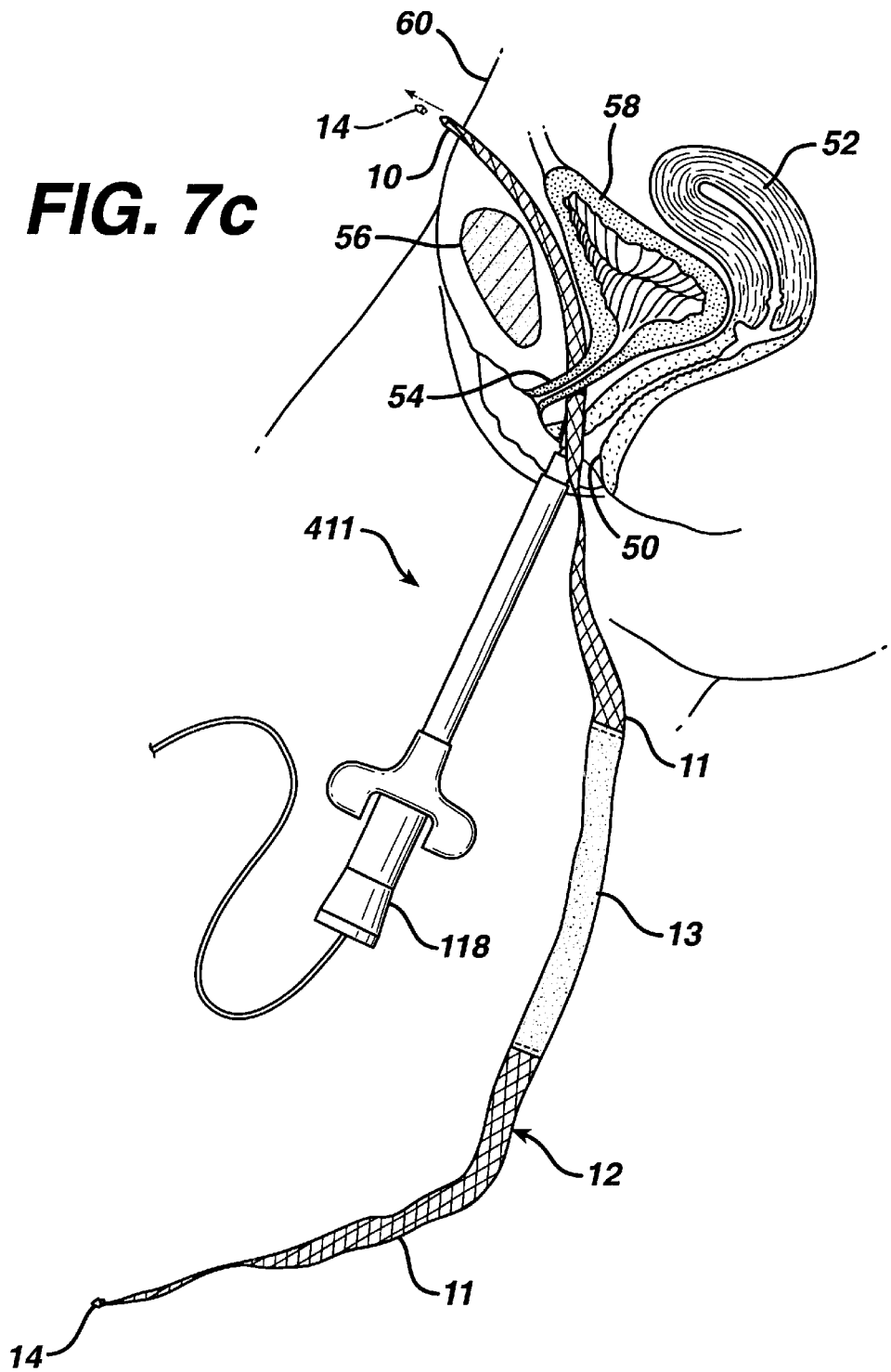
Figure 7D:
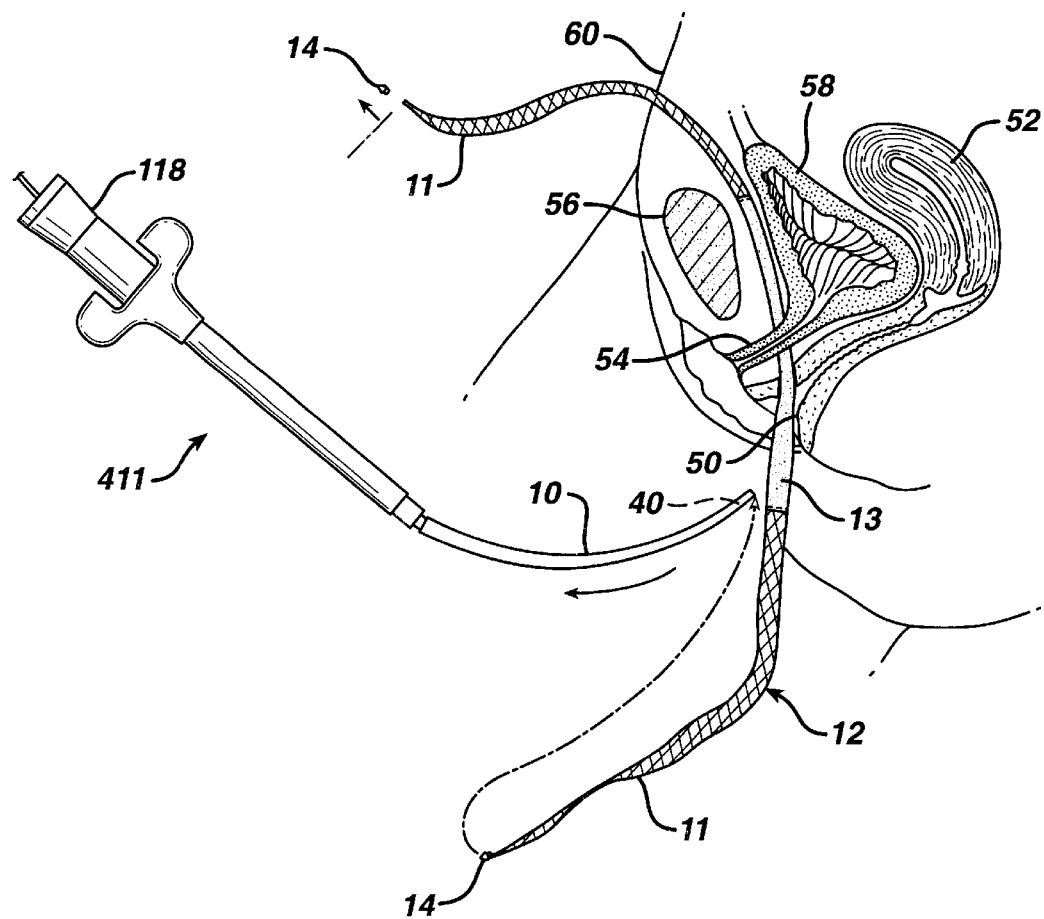
Figure 7E:
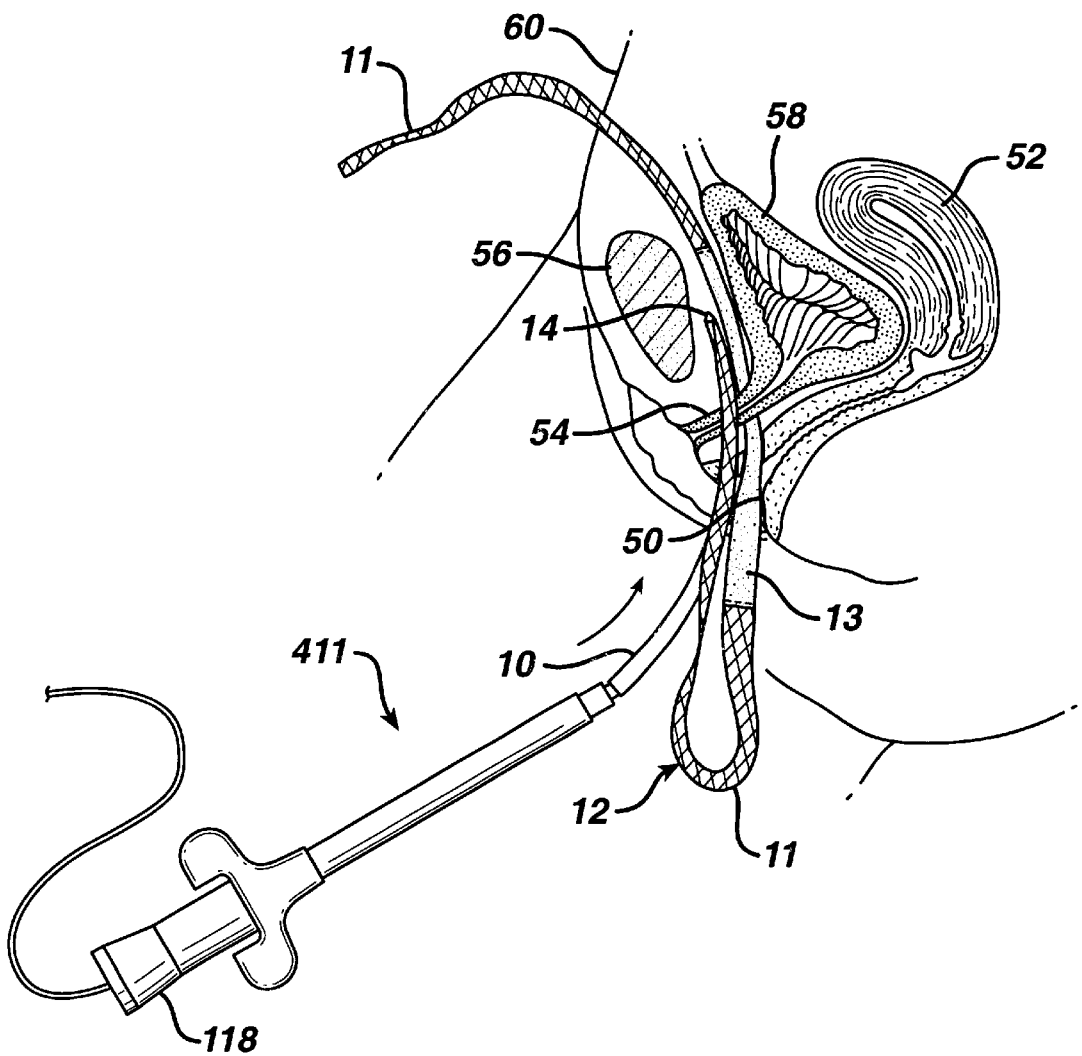
Figure 7F:
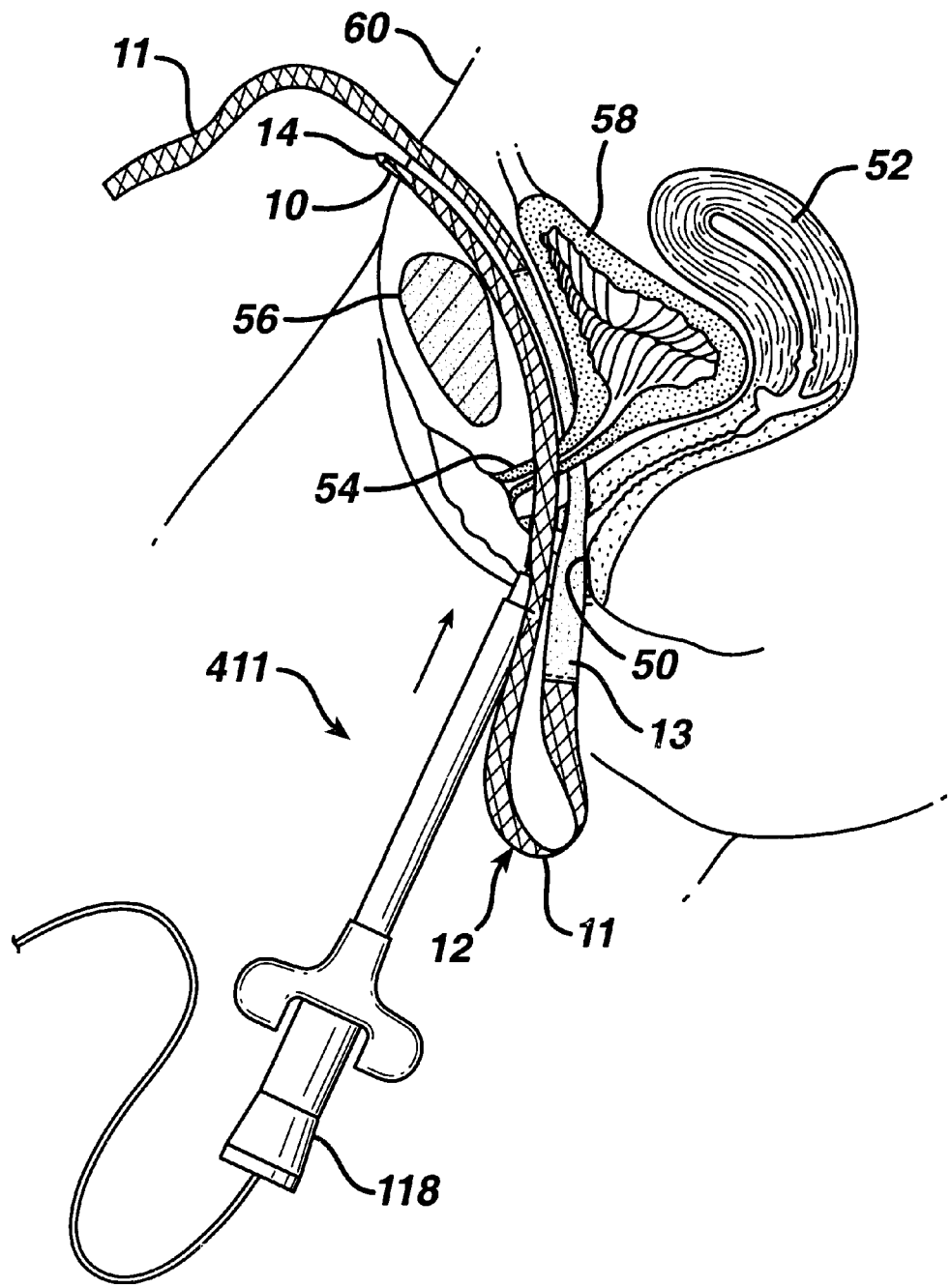
Figure 7G:
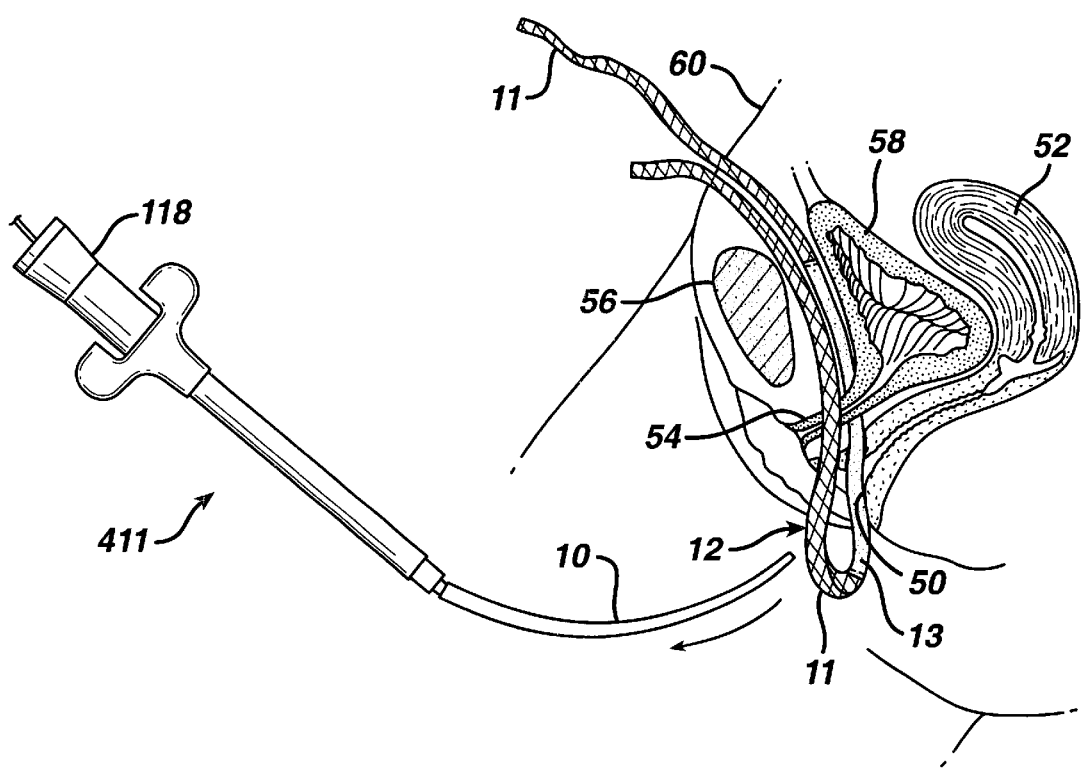
Figure 7H:
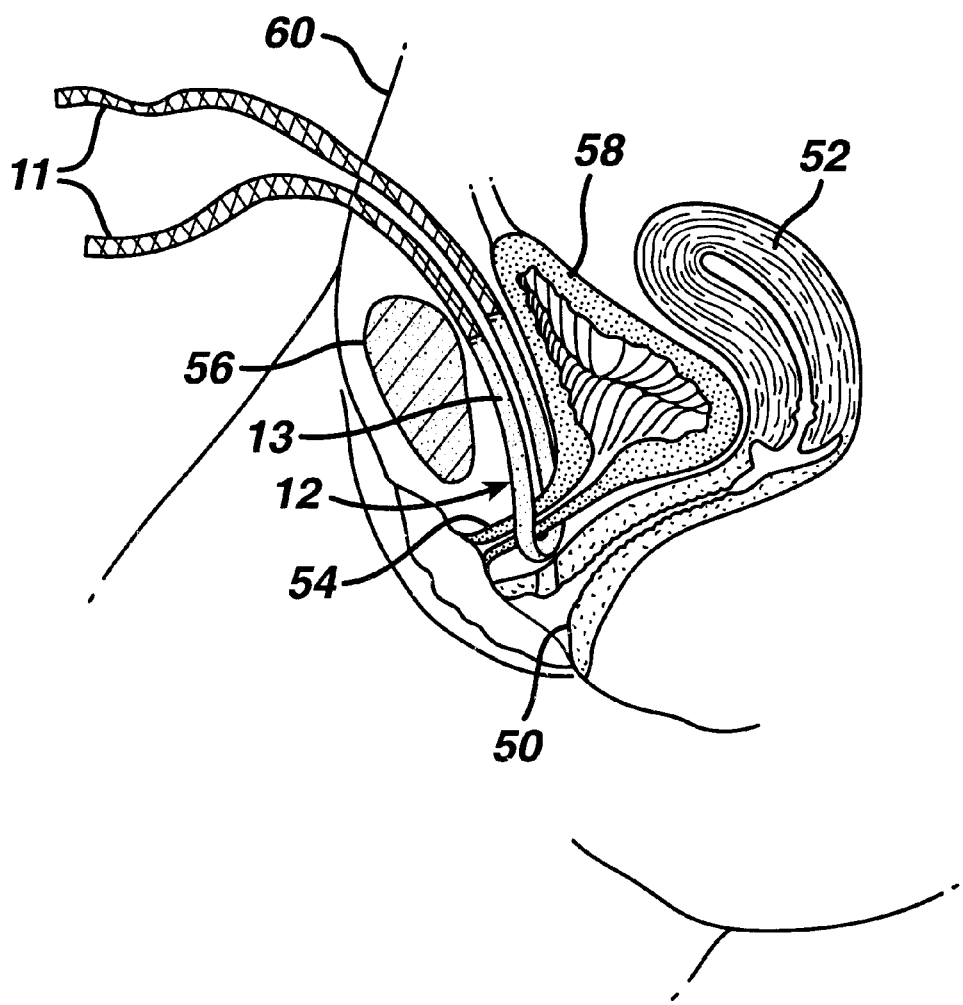

Since both procedures may be performed using a local anesthesia, the patient is able to provide feedback to the surgeon after tape 12 is in place. Typically, the urinary bladder 58 is filled with a fluid, such as water, using a catheter and the patient is requested to cough. The surgeon is able to determine the operation of the urethra and may adjust the tape 12, as necessary, by adjusting the ends of tape 12 located at the outside of the abdomen 60, FIGS. 6h and 7h. After adjustments, the surplus tape at the abdomen is cut off, and the ends of the tape are secured within the abdomen and the abdomen is closed. Likewise, the incision at the vaginal wall is closed whereby the tissue flap seals the tape between the urethra 54 and the wall of vagina 50.

Tape 12 is left in the body and forms an artificial ligament attached to the abdominal wall that provides the support for the urethra as required in order to restore urinary continence to the patient.

At the end of either procedure disclosed in FIGS. 6 and 7, the surgeon may perform a test procedure to determine the integrity of the urinary bladder. A hydraulic diagnosis of the bladder my be performed by placing a rigid endoscope/sheath transurethrally and injecting fluid through the sheath into the bladder. The bladder is pressurized to a known level, about 50 mm Hg as measured through the sheath. If the pressure is maintained, then the surgeon can be confident that the bladder has not been perforated. Conversely, if the bladder loses pressure, steps can be taken to repair any defects.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A surgical instrument for treating female urinary stress incontinence comprising:

a) a tape for implanting into a female patient's lower abdomen to provide support to the patient's urethra; and b) a curved needle element having a proximal end and a distal end and defining in part a conical tip and a curved shaft, the conical tip and curved shaft each defining a lumen for accepting a light transmitting means for transmitting images at the distal end to a viewing means external of the needle element.

2. The surgical instrument of claim 1 wherein the conical tip comprises a viewing port.

3. The surgical instrument of claim 1 wherein the conical tip is transparent.

4. The surgical instrument of claim 1 wherein the lumen extends from the distal end to the proximal end.

5. A surgical instrument for treating female urinary stress incontinence comprising:
   a) a curved needle element having a distal end and a proximal end and defining in part a curved shaft, the curved shaft defining a lumen for accepting a light transmitting means for transmitting images at the distal end to a viewing means external of the needle element.

6. The surgical instrument of claim 5 wherein the lumen extends from the distal end to the proximal end.

7. A surgical system for treating female urinary stress incontinence comprising:
   a. a tape for implanting into a female patient's lower abdomen to provide support to the patient's urethra;
   b. a curved needle element having a proximal end and a distal end and defining in part a curved shaft, the curved shaft defining a lumen for accepting an endoscope; and
   c. an optical system for transmitting images from the endoscope to a viewing means external of the needle element.

8. The surgical system of claim 7 wherein the optical system comprises a camera, a light source and a means for viewing images from the endoscope.

9. The surgical system of claim 7, wherein the needle element defines, at a distal tip, a conical tip.

10. The surgical system of claim 9, wherein the conical tip defines a viewing port.

11. The surgical system of claim 9, wherein the conical tip is transparent.

12. The surgical system of claim 7 wherein the lumen extends from the distal end to the proximal end.

13. A method for treating female urinary incontinence comprising the steps of:
   a) providing a first needle element and a second curved needle element and a tape attached at a first end to the first needle element and at a second end to the second needle element, each of the first and second needle elements defining in part a curved shaft and having a distal end and a proximal end, each of the first and second needle elements further defining a lumen for accepting a light transmitting means for transmitting images at the distal end to a viewing means external of the needle element;
   b) passing the first needle and tape into a female patient's body via the patient's vagina and on one side of the patient's urethra and extending the tape over the patient's public bone and through the patient's abdomen wall;
   c) passing the second needle element and tape into the patient's body via the patient's vagina and on an opposite side of the patient's urethra than the first needle element and extending the tape over the patient's pubic bone and through the patient's abdomen wall so that the tape thereby creates a supporting sling below the patient's urethra; and
   d) viewing images at the distal end of the first needle element during step (b) and the second needle element during step (c).

14. A method for treating female urinary incontinence comprising the steps of:
   a) providing a curved needle element having a tape attached thereto, the needle element defining in part a curved shaft and having a distal end and a proximal end, the needle element further defining a lumen for accepting a light transmitting means for transmitting images at the distal end to a viewing means external of the needle element;
   b) passing the needle element and tape into a patient's body via the patient's vagina to so that the tape thereby forms a sling around the patient's urethra; and
   c) viewing images at the distal end of the needle element.

15. A method for treating female urinary incontinence comprising the steps of:
   a) providing a curved needle element defining in part a curved shaft, the needle element defining a lumen for accepting a light transmitting means for transmitting images at the distal end to a viewing means external of the needle element;
   b) attaching a first end of a tape to the needle element;
   c) passing the needle element and tape into a patient's body;
   d) detaching the first end of the tape from the needle element;
   e) attaching a second end of the tape to the needle element and passing the needle element and tape into the patient's body to thereby form a sling around the patient's urethra; and
   e) viewing images at the distal end of the needle element.

16. A method for treating female urinary incontinence comprising the steps of:
   a. passing a tape into a patient's body via the patient's vagina to form a loop around the patient's urethra, the loop formed between the patient's vaginal wall and the patient's urethra and extending the tape over the pubic bone; and
   b. viewing images of the patient's tissue while passing the tape into the patient's body.

* * * * *

Disclaimer 6,475,139—Gary H. Miller, Milpitas, CA (US). VISUALLY-DIRECTED SURGICAL INSTRUMENT AND METHOD FOR TREATING FEMALE URINARY INCONTINENCE. Patent dated Nov. 5, 2002. Disclaimer filed Jul. 14, 2003, by the assignee, Ethicon, Inc.

Hereby enters this disclaimer to claims 1-16, of said patent.

*(Official Gazette, October 7, 2003)*